US006824995B1

(12) United States Patent
Wu

(10) Patent No.: US 6,824,995 B1
(45) Date of Patent: Nov. 30, 2004

(54) DIAGNOSTIC FOR METASTATIC PROSTATE CANCER

(75) Inventor: Guang-Jer Wu, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/653,961

(22) Filed: Sep. 1, 2000

Related U.S. Application Data

(63) Continuation of application No. PCT/US99/04850, filed on Mar. 2, 1999.
(60) Provisional application No. 60/076,664, filed on Mar. 3, 1998.

(51) Int. Cl.$^7$ .............................................. G01N 33/574
(52) U.S. Cl. ...................... 435/7.23; 530/350; 530/300; 530/387.1; 530/388.1; 435/7.1; 435/7.2; 435/7.21; 435/6; 424/9.1; 424/9.2; 204/450; 536/23.1; 536/23.4; 536/23.5; 536/24.33; 536/24.31
(58) Field of Search ................................ 435/7.2, 7.21, 435/7.23, 6, 7.1; 530/300, 350, 387.1, 388.1; 424/9.1, 9.2; 204/450; 536/23.1, 23.4, 23.5, 24.33, 24.31

(56) References Cited

U.S. PATENT DOCUMENTS

| 5,807,978 A | * | 9/1998 | Kokolus et al. ............. 530/300 |
| 6,057,105 A | * | 5/2000 | Hoon et al. ...................... 435/6 |
| 6,184,043 B1 | * | 2/2001 | Fodstad et al. .............. 436/526 |

FOREIGN PATENT DOCUMENTS

| WO | 9634117 A | 10/1996 | ............ C12Q/1/68 |
| WO | 9728193 A | 8/1997 | ........... C07K/16/32 |

OTHER PUBLICATIONS

Rubenstein, M, et al, 1989, Application of immunohistologic staining to develop a malignant index to aid in distinguishing benign from malignant prostatic tissue, Prostate, vol. 14, pp. 383–388.*
Shih, I–M, et al, 1994; Isolation and functional characterization of the A32 melanoma–associated antigen, Cancer Research, vol. 54, pp. 2514–2520.*
Liu, XH, et al, 1993, The prognostic value of the HNK–1 (Leu–7) antigen in prostatic cancer—an immunohistochemical study, Hinyokika Kiyo Acta Urologica Japonica, vol. 39, pp. 439–444.*
Filshie, RJ, et al, 1998, Leukemia, MUC18, a member of the immunoglobulin superfamily, is expressed on bone marrow fibroblasts and a subset of hematological malignanciesvol. 12, pp. 414–421.*
Shih, IM, et al, 1996, Diagnostic and biological implications of mel–CAM expression in mesenchymal neoplasms, Clinical Cancer Research, vol. 2, pp. 569–575.*

Kraus, A, et al, 1997, Analysis of the expression of intracellular adhesion molecule–1 and MUC18 on benign and malignant melanocytic lesions using monoclonal antibodies directed against distinct epitopes . . . , Melanoma Research, vol. 7, pp. s75–81.*
Swiss Protein Database, Accession No. P43121, MU18_Human Standard; PRT; 646 AA (Search Report US–09–653–961–2.rsp, result No. 1).*
Weninger, W, et al, 2000, Keratinocytes express the CD146 (Muc18/S–Endo) antigen in tissue culture and during inflammatory skin diseases, Journal of Investigative Dermatology, vol. 115, pp. 219–224.*
Hsu, M–Y, et al, 2000, E–cadherin expression in melanoma cells restores keratinocyte–mediated growth control and down–regulates expression of invasion–related adhesion receptors, American Journal of Pathology, vol. 156, pp. 1515–1525.*
Wu, G–J, et al, 2001, Prostate 48: 305–315.*
Wu GJ, et al. Gene. Nov. 14, 2001; 279 (1): 17–31.*
Brannen et al. (1975) "Specificity of Cell Membrane Antigens in Prostatic Cancer" *Cancer Chemotherapy Reports* vol. 59, No. 1:127–138.
Brannen et al. (unknown) "Specificity of Cell Membrane Antigens in Prostate Cancer" *National Cancer Institute Monograph* 49:251–253.
Catalona et al. (1978) "Carcinoma of the Prostate: A Review" *The Journal of Urology* 119:1–8.
Judith P. Johnson (1994) "Identification of Molecules Associated with the Development of Metastasis in Human Malignant Melanoma" *Invasion Metastasis* 14:123–130.
Johnson et al. (1996) "MUC18: A Cell Adhesion Molecule with a Potential Role in Tumor Growth and Tumor Cell Dissemination" *Current Topics in Microbiology and Immunology* 213:95–105.

(List continued on next page.)

*Primary Examiner*—Yvonne Eyler
*Assistant Examiner*—Stephen L. Rawlings
(74) *Attorney, Agent, or Firm*—Greenlee, Winner and Sullivan, P.C.

(57) ABSTRACT

The present disclosure provides methods for the diagnosis of metastatic prostate cancer and/or the prediction of the metastatic ability of prostate cancer in prostate biopsy tissue. Metastatic ability of prostate cancer is positively correlated with the level of transcriptional and translational expression of the MUC18 coding sequence in the neoplastic tissue. Methods for the determination of MUC18 protein synthesis include Western blots, ELISA, radioimmunoassay, immunofluorescence, and other immunoassays using MUC18-specific antibody and suitable detection means. Methods for measurement of transcriptional expression of the MUC18 coding sequence include Northern hybridizations and quantitative reverse transcriptase-polymerase chain reaction analyses. Absence of or very low MUC18 expression in the prostate tumor tissue is associated with nonmetastatic cancer, while relatively high levels of MUC18 expression are predictive of prostate cancer which is likely to metastasize or which has already metastasized. The present disclosure provides an improved diagnostic tool to aid the medical community in the choice of appropriate treatment regimens for prostate cancer patients.

5 Claims, 6 Drawing Sheets

OTHER PUBLICATIONS

Lehmann et al. (1989) "MUC18, a Marker of Tumor Progression in Human Melanoma, Shows Sequence Similarity to the Neural Cell Adhesion Molecules of the Immunoglobulin Superfamily" *Proc. Natl. Acad. Sci. USA* 86:9891–9895.

Luca, et al. (1993) "Direct Correlation Between MUC18 Expression and Metastatic Potential of Human Melanoma Cells" *Melanoma Research* 3:35–41.

Pantel, et al. (1995) "Early Metastasis of Human Solid Tumours: Expression of Cell Adhesion Molecules" *Cell Adhesion and Human Disease. Wiley, Chichester (Ciba Foundation Symposium 189)* 157–173.

Pickl, et al. (1997) "MUC18/MCAD (CD146), An Activation Antigen of Human T Lymphocytes [1,2]" *J. Immunol* 158:2107–15.

Rinker–Schaeffer, et al. (1993) "Molecular and Cellular Markers for Metastatic Prostate Cancer" *Cancer and Metastasis Reviews* 12:3–10.

Rummel, et al. (1996) "Phorbol Ester and Cyclic AMP–mediated Regulation of the Melanoma–associated Cell Adhesion Molecule MUC18/MCAM[1]" *Cancer Research* 56:2218–2223.

Shih, et al. (1997) "The Cell–Cell Adhesion Receptor Mel––CAM Acts as a Tumor Suppressor in Breast Carcinoma" *American Journal of Pathology* 151:745–751.

Tang, et al. (1994–95) "Adhesion Molecules and Tumor Metastasis: An Update" *Invasion Metastasis* 14:109–122.

Wood, et al. (1994) "Identification of Bone Marrow Micrometastases in Patients with Prostate Cancer" *Cancer* 74:2533–2540.

Xie, et al. (1997) "Expression of MCAM/MUC18 by Human Melanoma Cells Leads to Increased Tumor Growth and Metastasis[1]" *Cancer Research* 57:2295–2303.

* cited by examiner

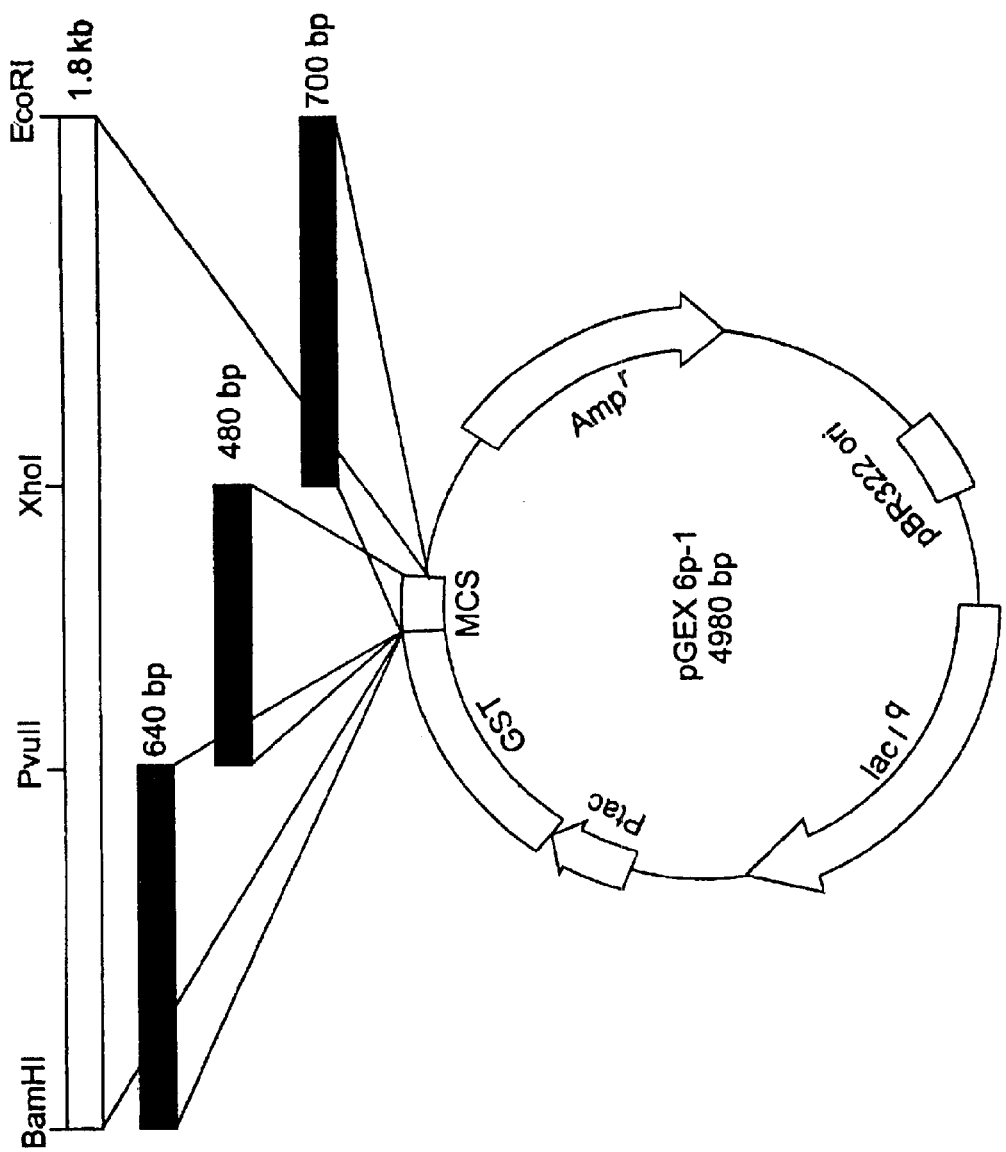
FIG. 1

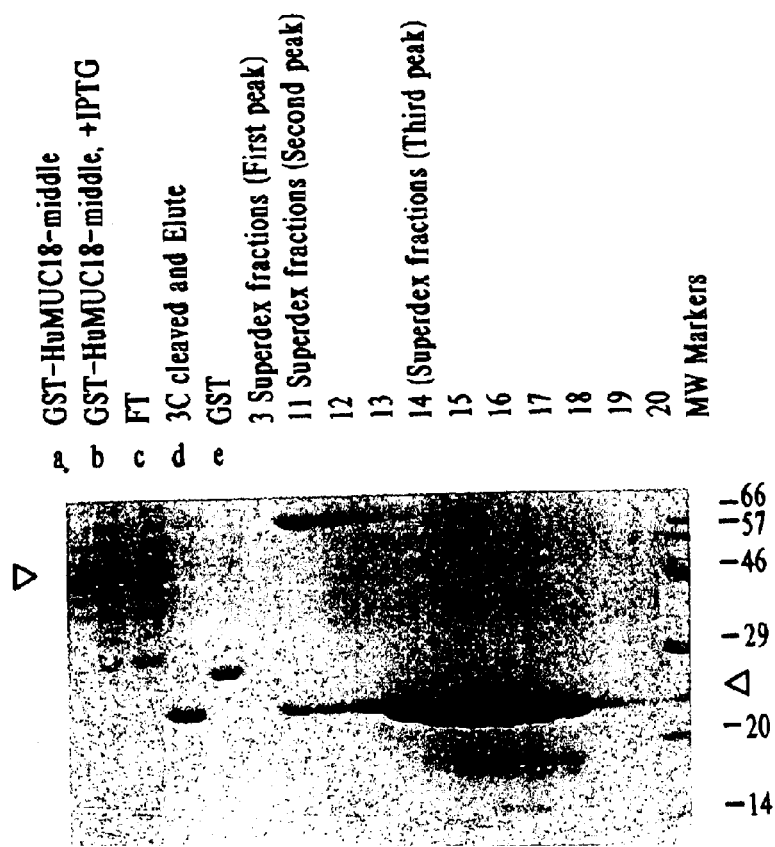
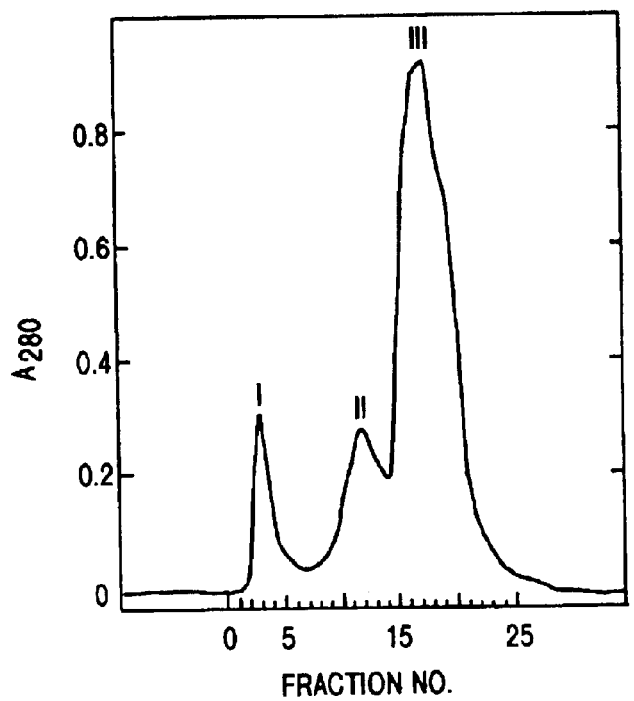
FIG. 3

SEQUENCE LISTING

```
<160> NUMBER OF SEQ ID NOS: 16

<210> SEQ ID NO 1
<211> LENGTH: 1950
<212> TYPE: DNA
<213> ORGANISM: Homo sapiens
<220> FEATURE:
<221> NAME/KEY: CDS
<222> LOCATION: (1)..(1938)

<400> SEQUENCE: 1 atg ggg ctt ccc agg ctg gtc tgc gcc ttc ttg ctc gcc gcc tgc tgc      48
Met Gly Leu Pro Arg Leu Val Cys Ala Phe Leu Leu Ala Ala Cys Cys
 1               5                  10                  15 tgc tgt cct cgc gtc gcg ggt gtg ccc gga gag gct gag cag cct gcg      96
Cys Cys Pro Arg Val Ala Gly Val Pro Gly Glu Ala Glu Gln Pro Ala
            20                  25                  30 cct gag ctg gtg gag gtg gaa gtg ggc agc aca gcc ctt ctg aag tgc     144
Pro Glu Leu Val Glu Val Glu Val Gly Ser Thr Ala Leu Leu Lys Cys
        35                  40                  45
```

```
ggc ctc tcc cag tcc caa ggc aac ctc agc cat gtc gac tgg ttt tct    192
Gly Leu Ser Gln Ser Gln Gly Asn Leu Ser His Val Asp Trp Phe Ser
     50              55                  60 gtc cac aag gag aag cgg acg ctc atc ttc cgt gtg cgc cag ggc cag    240
Val His Lys Glu Lys Arg Thr Leu Ile Phe Arg Val Arg Gln Gly Gln
 65              70                  75                  80 ggc cag agc gaa cct ggg gag tac gag cag cgg ctc agc ctc cag gac    288
Gly Gln Ser Glu Pro Gly Glu Tyr Glu Gln Arg Leu Ser Leu Gln Asp
                 85                  90                  95 aga ggg gct act ctg gcc ctg act caa gtc acc ccc caa gac gag cgc    336
Arg Gly Ala Thr Leu Ala Leu Thr Gln Val Thr Pro Gln Asp Glu Arg
            100                 105                 110 atc ttc ttg tgc cag ggc aag cgc cct cgg tcc cag gag tac cgc atc    384
Ile Phe Leu Cys Gln Gly Lys Arg Pro Arg Ser Gln Glu Tyr Arg Ile
        115                 120                 125 cag ctc cgc gtc tac aaa gct ccg gag gag cca aac atc cag gtc aac    432
Gln Leu Arg Val Tyr Lys Ala Pro Glu Glu Pro Asn Ile Gln Val Asn
    130                 135                 140 ccc ctg ggc atc cct gtg aac agt aag gag cct gag gag gtc gct acc    480
Pro Leu Gly Ile Pro Val Asn Ser Lys Glu Pro Glu Glu Val Ala Thr
145                 150                 155                 160 tgt gta ggg agg aac ggg tac ccc att cct caa gtc atc tgg tac aag    528
Cys Val Gly Arg Asn Gly Tyr Pro Ile Pro Gln Val Ile Trp Tyr Lys
                165                 170                 175 aat ggc cgg cct ctg aag gag gag aag aac cgg gtc cac att cag tcg    576
Asn Gly Arg Pro Leu Lys Glu Glu Lys Asn Arg Val His Ile Gln Ser
            180                 185                 190 tcc cag act gtg gag tcg agt ggt ttg tac acc ttg cag agt att ctg    624
Ser Gln Thr Val Glu Ser Ser Gly Leu Tyr Thr Leu Gln Ser Ile Leu
        195                 200                 205 aag gca cag ctg gtt aaa gaa gac aaa gat gcc cag ttt tac tgt gag    672
Lys Ala Gln Leu Val Lys Glu Asp Lys Asp Ala Gln Phe Tyr Cys Glu
    210                 215                 220 ctc aac tac cgg ctg ccc agt ggg aac cac atg aag gag tcc agg gaa    720
Leu Asn Tyr Arg Leu Pro Ser Gly Asn His Met Lys Glu Ser Arg Glu
225                 230                 235                 240 gtc acc gtc cct gtt ttc tac ccg aca gaa aaa gtg tgg ctg gaa gtg    768
Val Thr Val Pro Val Phe Tyr Pro Thr Glu Lys Val Trp Leu Glu Val
                245                 250                 255 gag ccc gtg gga atg ctg aag gaa ggg gac cgc gtg gaa atc agg tgt    816
Glu Pro Val Gly Met Leu Lys Glu Gly Asp Arg Val Glu Ile Arg Cys
            260                 265                 270 ttg gct gat ggc aac cct cca cca cac ttc agc atc agc aag cag aac    864
Leu Ala Asp Gly Asn Pro Pro Pro His Phe Ser Ile Ser Lys Gln Asn
        275                 280                 285 ccc agc acc agg gag gca gag gaa gag aca acc aac gac aac ggg gtc    912
Pro Ser Thr Arg Glu Ala Glu Glu Glu Thr Thr Asn Asp Asn Gly Val
    290                 295                 300 ctg gtg ctg gag cct gcc cgg aag gaa cac agt ggg cgc tat gaa tgt    960
Leu Val Leu Glu Pro Ala Arg Lys Glu His Ser Gly Arg Tyr Glu Cys
305                 310                 315                 320 cag ggc ctg gac ttg gac acc atg ata tcg ctg ctg agt gaa cca cag   1008
Gln Gly Leu Asp Leu Asp Thr Met Ile Ser Leu Leu Ser Glu Pro Gln
                325                 330                 335 gaa cta ctg gtg aac tat gtg tct gac gtc cga gtg agt ccc gca gcc   1056
Glu Leu Leu Val Asn Tyr Val Ser Asp Val Arg Val Ser Pro Ala Ala
            340                 345                 350 cct gag aga cag gaa ggc agc agc ctc acc ctg acc tgt gag gca gag   1104
Pro Glu Arg Gln Glu Gly Ser Ser Leu Thr Leu Thr Cys Glu Ala Glu
```

```
                355                 360                 365
agt agc cag gac ctc gag ttc cag tgg ctg aga gaa gag aca ggc cag    1152
Ser Ser Gln Asp Leu Glu Phe Gln Trp Leu Arg Glu Glu Thr Gly Gln
    370                 375                 380 gtg ctg gaa agg ggg cct gtg ctt cag ttg cat gac ctg aaa cgg gag    1200
Val Leu Glu Arg Gly Pro Val Leu Gln Leu His Asp Leu Lys Arg Glu
385                 390                 395                 400 gca gga ggc ggc tat cgc tgc gtg gcg tct gtg ccc agc ata ccc gga    1248
Ala Gly Gly Gly Tyr Arg Cys Val Ala Ser Val Pro Ser Ile Pro Gly
                405                 410                 415 ctg aac cgc aca cag ctg gtc aac gtg gcc att ttt ggc ccc cct tgg    1296
Leu Asn Arg Thr Gln Leu Val Asn Val Ala Ile Phe Gly Pro Pro Trp
            420                 425                 430 atg gca ttc aag gag agg aag gtg tgg gtg aaa gag aat atg gtg ttg    1344
Met Ala Phe Lys Glu Arg Lys Val Trp Val Lys Glu Asn Met Val Leu
        435                 440                 445 aat ctg tct tgt gaa gcg tca ggg cac ccc cgg ccc acc atc tcc tgg    1392
Asn Leu Ser Cys Glu Ala Ser Gly His Pro Arg Pro Thr Ile Ser Trp
    450                 455                 460 aac gtc aac ggc acg gca agt gaa caa gac caa gat cca cag cga gtc    1440
Asn Val Asn Gly Thr Ala Ser Glu Gln Asp Gln Asp Pro Gln Arg Val
465                 470                 475                 480 ctg agc acc ctg aat gtc ctc gtg acc ccg gag ctg ttg gag aca ggt    1488
Leu Ser Thr Leu Asn Val Leu Val Thr Pro Glu Leu Leu Glu Thr Gly
                485                 490                 495 gtt gaa tgc acg gcc tcc aac gac ctg ggc aaa aac acc agc atc ctc    1536
Val Glu Cys Thr Ala Ser Asn Asp Leu Gly Lys Asn Thr Ser Ile Leu
            500                 505                 510 ttc ctg gag ctg gtc aat tta acc acc ctc aca cca gac tcc aac aca    1584
Phe Leu Glu Leu Val Asn Leu Thr Thr Leu Thr Pro Asp Ser Asn Thr
        515                 520                 525 acc act ggc ctc agc act tcc act gcc agt cct cat acc aga gcc aac    1632
Thr Thr Gly Leu Ser Thr Ser Thr Ala Ser Pro His Thr Arg Ala Asn
    530                 535                 540 agc acc tcc aca gag aga aag ctg ccg gag ccg gag agc cgg ggc gtg    1680
Ser Thr Ser Thr Glu Arg Lys Leu Pro Glu Pro Glu Ser Arg Gly Val
545                 550                 555                 560 gtc atc gtg gct gtg att gtg tgc atc ctg gtc ctg gcg gtg ctg ggc    1728
Val Ile Val Ala Val Ile Val Cys Ile Leu Val Leu Ala Val Leu Gly
                565                 570                 575 gct gtc ctc tat ttc ctc tat aag aag ggc aag ctg ccg tgc agg cgc    1776
Ala Val Leu Tyr Phe Leu Tyr Lys Lys Gly Lys Leu Pro Cys Arg Arg
            580                 585                 590 tca ggg aag cag gag atc acg ctg ccc ccg tct cgt aag agc gaa ctt    1824
Ser Gly Lys Gln Glu Ile Thr Leu Pro Pro Ser Arg Lys Ser Glu Leu
        595                 600                 605 gta gtt gaa gtt aag tca gat aag ctc cca gaa gag atg ggc ctc ctg    1872
Val Val Glu Val Lys Ser Asp Lys Leu Pro Glu Glu Met Gly Leu Leu
    610                 615                 620 cag ggc agc agc ggt gac aag agg gct ccg gga gac cag gga gag aaa    1920
Gln Gly Ser Ser Gly Asp Lys Arg Ala Pro Gly Asp Gln Gly Glu Lys
625                 630                 635                 640 tac atc gat ctg agg cat tagccccgaa at                              1950
Tyr Ile Asp Leu Arg His
                645

<210> SEQ ID NO 2
<211> LENGTH: 646
<212> TYPE: PRT
<213> ORGANISM: Homo sapiens
```

<400> SEQUENCE: 2

```
Met Gly Leu Pro Arg Leu Val Cys Ala Phe Leu Leu Ala Ala Cys Cys
 1               5                  10                  15
Cys Cys Pro Arg Val Ala Gly Val Pro Gly Glu Ala Glu Gln Pro Ala
             20                  25                  30
Pro Glu Leu Val Glu Val Glu Val Gly Ser Thr Ala Leu Leu Lys Cys
         35                  40                  45
Gly Leu Ser Gln Ser Gln Gly Asn Leu Ser His Val Asp Trp Phe Ser
     50                  55                  60
Val His Lys Glu Lys Arg Thr Leu Ile Phe Arg Val Arg Gln Gly Gln
 65                  70                  75                  80
Gly Gln Ser Glu Pro Gly Glu Tyr Glu Gln Arg Leu Ser Leu Gln Asp
                 85                  90                  95
Arg Gly Ala Thr Leu Ala Leu Thr Gln Val Thr Pro Gln Asp Glu Arg
            100                 105                 110
Ile Phe Leu Cys Gln Gly Lys Arg Pro Arg Ser Gln Glu Tyr Arg Ile
        115                 120                 125
Gln Leu Arg Val Tyr Lys Ala Pro Glu Glu Pro Asn Ile Gln Val Asn
    130                 135                 140
Pro Leu Gly Ile Pro Val Asn Ser Lys Glu Pro Glu Glu Val Ala Thr
145                 150                 155                 160
Cys Val Gly Arg Asn Gly Tyr Pro Ile Pro Gln Val Ile Trp Tyr Lys
                165                 170                 175
Asn Gly Arg Pro Leu Lys Glu Glu Lys Asn Arg Val His Ile Gln Ser
            180                 185                 190
Ser Gln Thr Val Glu Ser Ser Gly Leu Tyr Thr Leu Gln Ser Ile Leu
        195                 200                 205
Lys Ala Gln Leu Val Lys Glu Asp Lys Asp Ala Gln Phe Tyr Cys Glu
    210                 215                 220
Leu Asn Tyr Arg Leu Pro Ser Gly Asn His Met Lys Glu Ser Arg Glu
225                 230                 235                 240
Val Thr Val Pro Val Phe Tyr Pro Thr Glu Lys Val Trp Leu Glu Val
                245                 250                 255
Glu Pro Val Gly Met Leu Lys Glu Gly Asp Arg Val Glu Ile Arg Cys
            260                 265                 270
Leu Ala Asp Gly Asn Pro Pro His Phe Ser Ile Ser Lys Gln Asn
    275                 280                 285
Pro Ser Thr Arg Glu Ala Glu Glu Thr Thr Asn Asp Asn Gly Val
    290                 295                 300
Leu Val Leu Glu Pro Ala Arg Lys Glu His Ser Gly Arg Tyr Glu Cys
305                 310                 315                 320
Gln Gly Leu Asp Leu Asp Thr Met Ile Ser Leu Leu Ser Glu Pro Gln
                325                 330                 335
Glu Leu Leu Val Asn Tyr Val Ser Asp Val Arg Val Ser Pro Ala Ala
            340                 345                 350
Pro Glu Arg Gln Glu Gly Ser Ser Leu Thr Leu Thr Cys Glu Ala Glu
        355                 360                 365
Ser Ser Gln Asp Leu Glu Phe Gln Trp Leu Arg Glu Glu Thr Gly Gln
    370                 375                 380
Val Leu Glu Arg Gly Pro Val Leu Gln Leu His Asp Leu Lys Arg Glu
385                 390                 395                 400
Ala Gly Gly Gly Tyr Arg Cys Val Ala Ser Val Pro Ser Ile Pro Gly
```

```
                    405                 410                 415
Leu Asn Arg Thr Gln Leu Val Asn Val Ala Ile Phe Gly Pro Pro Trp
            420                 425                 430
Met Ala Phe Lys Glu Arg Lys Val Trp Val Lys Glu Asn Met Val Leu
        435                 440                 445
Asn Leu Ser Cys Glu Ala Ser Gly His Pro Arg Pro Thr Ile Ser Trp
    450                 455                 460
Asn Val Asn Gly Thr Ala Ser Glu Gln Asp Gln Asp Pro Gln Arg Val
465                 470                 475                 480
Leu Ser Thr Leu Asn Val Leu Val Thr Pro Glu Leu Leu Glu Thr Gly
                485                 490                 495
Val Glu Cys Thr Ala Ser Asn Asp Leu Gly Lys Asn Thr Ser Ile Leu
            500                 505                 510
Phe Leu Glu Leu Val Asn Leu Thr Thr Leu Thr Pro Asp Ser Asn Thr
        515                 520                 525
Thr Thr Gly Leu Ser Thr Ser Thr Ala Ser Pro His Thr Arg Ala Asn
    530                 535                 540
Ser Thr Ser Thr Glu Arg Lys Leu Pro Glu Pro Glu Ser Arg Gly Val
545                 550                 555                 560
Val Ile Val Ala Val Ile Val Cys Ile Leu Val Leu Ala Val Leu Gly
                565                 570                 575
Ala Val Leu Tyr Phe Leu Tyr Lys Lys Gly Lys Leu Pro Cys Arg Arg
            580                 585                 590
Ser Gly Lys Gln Glu Ile Thr Leu Pro Pro Ser Arg Lys Ser Glu Leu
        595                 600                 605
Val Val Glu Val Lys Ser Asp Lys Leu Pro Glu Glu Met Gly Leu Leu
    610                 615                 620
Gln Gly Ser Ser Gly Asp Lys Arg Ala Pro Gly Asp Gln Gly Glu Lys
625                 630                 635                 640
Tyr Ile Asp Leu Arg His
                645

<210> SEQ ID NO 3
<211> LENGTH: 1960
<212> TYPE: DNA
<213> ORGANISM: Homo sapiens
<220> FEATURE:
<221> NAME/KEY: CDS
<222> LOCATION: (8)..(1945)

<400> SEQUENCE: 3 gggaagc atg ggg ctt ccc agg ctg gtc tgc gcc ttc ttg ctc gcc gcc        49
        Met Gly Leu Pro Arg Leu Val Cys Ala Phe Leu Leu Ala Ala
        1               5                   10 tgc tgc tgc tgt cct cgc gtc gcg ggt gtg ccc gga gag gct gag cag        97
Cys Cys Cys Cys Pro Arg Val Ala Gly Val Pro Gly Glu Ala Glu Gln
15                  20                  25                  30 cct gcg cct gag ctg gtg gag gtg gaa gtg ggc agc aca gcc ctt ctg       145
Pro Ala Pro Glu Leu Val Glu Val Glu Val Gly Ser Thr Ala Leu Leu
                35                  40                  45 aag tgc ggc ctc tcc cag tcc caa ggc aac ctc agc cat gtc gac tgg       193
Lys Cys Gly Leu Ser Gln Ser Gln Gly Asn Leu Ser His Val Asp Trp
            50                  55                  60 ttt tct gtc cac aag gag aag cgg acg ctc atc ttc cgt gtg cgc cag       241
Phe Ser Val His Lys Glu Lys Arg Thr Leu Ile Phe Arg Val Arg Gln
        65                  70                  75 ggc cag ggc cag agc gaa cct ggg gag tac gag cag cgg ctc agc ctc       289
```

```
                    -continued

Gly Gln Gly Gln Ser Glu Pro Gly Glu Tyr Glu Gln Arg Leu Ser Leu
    80                  85                  90 cag gac aga ggg gct act ctg gcc ctg act caa gtc acc ccc caa gac        337
Gln Asp Arg Gly Ala Thr Leu Ala Leu Thr Gln Val Thr Pro Gln Asp
95                  100                 105                 110 gag cgc atc ttc ttg tgc cag ggc aag cgc cct cgg tcc cag gag tac        385
Glu Arg Ile Phe Leu Cys Gln Gly Lys Arg Pro Arg Ser Gln Glu Tyr
                115                 120                 125 cgc atc cag ctc cgc gtc tac aaa gct ccg gag gag cca aac atc cag        433
Arg Ile Gln Leu Arg Val Tyr Lys Ala Pro Glu Glu Pro Asn Ile Gln
            130                 135                 140 gtc aac ccc ctg ggc atc cct gtg aac agt aag gag cct gag gag gtc        481
Val Asn Pro Leu Gly Ile Pro Val Asn Ser Lys Glu Pro Glu Glu Val
        145                 150                 155 gct acc tgt gta ggg agg aac ggg tac ccc att cct caa gtc atc tgg        529
Ala Thr Cys Val Gly Arg Asn Gly Tyr Pro Ile Pro Gln Val Ile Trp
    160                 165                 170 tac aag aat ggc cgg cct ctg aag gag gag aag aac cgg gtc cac att        577
Tyr Lys Asn Gly Arg Pro Leu Lys Glu Glu Lys Asn Arg Val His Ile
175                 180                 185                 190 cag tcg tcc cag act gtg gag tcg agt ggt ttg tac acc ttg cag agt        625
Gln Ser Ser Gln Thr Val Glu Ser Ser Gly Leu Tyr Thr Leu Gln Ser
                195                 200                 205 att ctg aag gca cag ctg gtt aaa gaa gac aaa gat gcc cag ttt tac        673
Ile Leu Lys Ala Gln Leu Val Lys Glu Asp Lys Asp Ala Gln Phe Tyr
            210                 215                 220 tgt gag ctc aac tac cgg ctg ccc agt ggg aac cac atg aag gag tcc        721
Cys Glu Leu Asn Tyr Arg Leu Pro Ser Gly Asn His Met Lys Glu Ser
        225                 230                 235 agg gaa gtc acc gtc cct gtt ttc tac ccg aca gaa aaa gtg tgg ctg        769
Arg Glu Val Thr Val Pro Val Phe Tyr Pro Thr Glu Lys Val Trp Leu
    240                 245                 250 gaa gtg gag ccc gtg gga atg ctg aag gaa ggg gac cgc gtg gaa atc        817
Glu Val Glu Pro Val Gly Met Leu Lys Glu Gly Asp Arg Val Glu Ile
255                 260                 265                 270 agg tgt ttg gct gat ggc aac cct cca cca cac ttc agc atc agc aag        865
Arg Cys Leu Ala Asp Gly Asn Pro Pro Pro His Phe Ser Ile Ser Lys
                275                 280                 285 cag aac ccc agc acc agg gag gca gag gaa gag aca acc aac gac aac        913
Gln Asn Pro Ser Thr Arg Glu Ala Glu Glu Glu Thr Thr Asn Asp Asn
            290                 295                 300 ggg gtc ctg gtg ctg gag cct gcc cgg aag gaa cac agt ggg cgc tat        961
Gly Val Leu Val Leu Glu Pro Ala Arg Lys Glu His Ser Gly Arg Tyr
        305                 310                 315 gaa tgt cag gcc tgg aac ttg gac acc atg ata tcg ctg ctg agt gaa       1009
Glu Cys Gln Ala Trp Asn Leu Asp Thr Met Ile Ser Leu Leu Ser Glu
    320                 325                 330 cca cag gaa cta ctg gtg aac tat gtg tct gac gtc cga gtg agt ccc       1057
Pro Gln Glu Leu Leu Val Asn Tyr Val Ser Asp Val Arg Val Ser Pro
335                 340                 345                 350 gca gcc cct gag aga cag gaa ggc agc agc ctc acc ctg acc tgt gag       1105
Ala Ala Pro Glu Arg Gln Glu Gly Ser Ser Leu Thr Leu Thr Cys Glu
                355                 360                 365 gca gag agt agc cag gac ctc gag ttc cag tgg ctg aga gaa gag aca       1153
Ala Glu Ser Ser Gln Asp Leu Glu Phe Gln Trp Leu Arg Glu Glu Thr
            370                 375                 380 gac cag gtg ctg gaa agg ggg cct gtg ctt cag ttg cat gac ctg aaa       1201
Asp Gln Val Leu Glu Arg Gly Pro Val Leu Gln Leu His Asp Leu Lys
        385                 390                 395
```

```
cgg gag gca gga ggc ggc tat cgc tgc gtg gcg tct gtg ccc agc ata    1249
Arg Glu Ala Gly Gly Gly Tyr Arg Cys Val Ala Ser Val Pro Ser Ile
    400                 405                 410 ccc ggc ctg aac cgc aca cag ctg gtc aag ctg gcc att ttt ggc ccc    1297
Pro Gly Leu Asn Arg Thr Gln Leu Val Lys Leu Ala Ile Phe Gly Pro
415                 420                 425                 430 cct tgg atg gca ttc aag gag agg aag gtg tgg gtg aaa gag aat atg    1345
Pro Trp Met Ala Phe Lys Glu Arg Lys Val Trp Val Lys Glu Asn Met
                435                 440                 445 gtg ttg aat ctg tct tgt gaa gcg tca ggg cac ccc cgg ccc acc atc    1393
Val Leu Asn Leu Ser Cys Glu Ala Ser Gly His Pro Arg Pro Thr Ile
            450                 455                 460 tcc tgg aac gtc aac ggc acg gca agt gaa caa gac caa gat cca cag    1441
Ser Trp Asn Val Asn Gly Thr Ala Ser Glu Gln Asp Gln Asp Pro Gln
        465                 470                 475 cga gtc ctg agc acc ctg aat gtc ctc gtg acc ccg gag ctg ttg gag    1489
Arg Val Leu Ser Thr Leu Asn Val Leu Val Thr Pro Glu Leu Leu Glu
    480                 485                 490 aca ggt gtt gaa tgc acg gcc tcc aac gac ctg ggc aaa aac acc agc    1537
Thr Gly Val Glu Cys Thr Ala Ser Asn Asp Leu Gly Lys Asn Thr Ser
495                 500                 505                 510 atc ctc ttc ctg gag ctg gtc aat tta acc acc ctc aca cca gac tcc    1585
Ile Leu Phe Leu Glu Leu Val Asn Leu Thr Thr Leu Thr Pro Asp Ser
                515                 520                 525 aac aca acc act ggc ctc agc act tcc act gcc agt cct cat acc aga    1633
Asn Thr Thr Thr Gly Leu Ser Thr Ser Thr Ala Ser Pro His Thr Arg
            530                 535                 540 gcc aac agc acc tcc aca gag aga aag ctg ccg gag ccg gag agc cgg    1681
Ala Asn Ser Thr Ser Thr Glu Arg Lys Leu Pro Glu Pro Glu Ser Arg
        545                 550                 555 ggc gtg gtc atc gtg gct gtg att gtg tgc atc ctg gtc ctg gcg gtg    1729
Gly Val Val Ile Val Ala Val Ile Val Cys Ile Leu Val Leu Ala Val
    560                 565                 570 ctg ggc gct gtc ctc tat ttc ctc tat aag aag ggc aag ctg ccg tgc    1777
Leu Gly Ala Val Leu Tyr Phe Leu Tyr Lys Lys Gly Lys Leu Pro Cys
575                 580                 585                 590 agg cgc tca ggg aag cag gag atc acg ctg ccc ccg tct cgt aag acc    1825
Arg Arg Ser Gly Lys Gln Glu Ile Thr Leu Pro Pro Ser Arg Lys Thr
                595                 600                 605 gaa ctt gta gtt gaa gtt aag tca gat aag ctc cca gaa gag atg ggc    1873
Glu Leu Val Val Glu Val Lys Ser Asp Lys Leu Pro Glu Glu Met Gly
            610                 615                 620 ctc ctg cag ggc agc agc ggt gac aag agg gct ccg gga gac cag gga    1921
Leu Leu Gln Gly Ser Ser Gly Asp Lys Arg Ala Pro Gly Asp Gln Gly
        625                 630                 635 gag aaa tac atc gat ctg agg cat tagccccgaa tcact                   1960
Glu Lys Tyr Ile Asp Leu Arg His
    640                 645
```

<210> SEQ ID NO 4
<211> LENGTH: 646
<212> TYPE: PRT
<213> ORGANISM: Homo sapiens

<400> SEQUENCE: 4

```
Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
```

-continued

```
                35                  40                  45
Gly Leu Ser Gln Ser Gln Gly Asn Leu Ser His Val Asp Trp Phe Ser
         50                  55                  60
Val His Lys Glu Lys Arg Thr Leu Ile Phe Arg Val Arg Gln Gly Gln
 65                  70                  75                  80
Gly Gln Ser Glu Pro Gly Glu Tyr Glu Gln Arg Leu Ser Leu Gln Asp
                 85                  90                  95
Arg Gly Ala Thr Leu Ala Leu Thr Gln Val Thr Pro Gln Asp Glu Arg
                100                 105                 110
Ile Phe Leu Cys Gln Gly Lys Arg Pro Arg Ser Gln Glu Tyr Arg Ile
                115                 120                 125
Gln Leu Arg Val Tyr Lys Ala Pro Glu Glu Pro Asn Ile Gln Val Asn
        130                 135                 140
Pro Leu Gly Ile Pro Val Asn Ser Lys Glu Pro Glu Val Ala Thr
145                 150                 155                 160
Cys Val Gly Arg Asn Gly Tyr Pro Ile Pro Gln Val Ile Trp Tyr Lys
                165                 170                 175
Asn Gly Arg Pro Leu Lys Glu Lys Asn Arg Val His Ile Gln Ser
        180                 185                 190
Ser Gln Thr Val Glu Ser Ser Gly Leu Tyr Thr Leu Gln Ser Ile Leu
        195                 200                 205
Lys Ala Gln Leu Val Lys Glu Asp Lys Asp Ala Gln Phe Tyr Cys Glu
        210                 215                 220
Leu Asn Tyr Arg Leu Pro Ser Gly Asn His Met Lys Glu Ser Arg Glu
225                 230                 235                 240
Val Thr Val Pro Val Phe Tyr Pro Thr Glu Lys Val Trp Leu Glu Val
                245                 250                 255
Glu Pro Val Gly Met Leu Lys Glu Gly Asp Arg Val Glu Ile Arg Cys
                260                 265                 270
Leu Ala Asp Gly Asn Pro Pro His Phe Ser Ile Ser Lys Gln Asn
        275                 280                 285
Pro Ser Thr Arg Glu Ala Glu Glu Thr Thr Asn Asp Asn Gly Val
        290                 295                 300
Leu Val Leu Glu Pro Ala Arg Lys Glu His Ser Gly Arg Tyr Glu Cys
305                 310                 315                 320
Gln Ala Trp Asn Leu Asp Thr Met Ile Ser Leu Ser Glu Pro Gln
                325                 330                 335
Glu Leu Leu Val Asn Tyr Val Ser Asp Val Arg Val Ser Pro Ala Ala
        340                 345                 350
Pro Glu Arg Gln Glu Gly Ser Ser Leu Thr Leu Thr Cys Glu Ala Glu
        355                 360                 365
Ser Ser Gln Asp Leu Glu Phe Gln Trp Leu Arg Glu Glu Thr Asp Gln
        370                 375                 380
Val Leu Glu Arg Gly Pro Val Leu Gln Leu His Asp Leu Lys Arg Glu
385                 390                 395                 400
Ala Gly Gly Gly Tyr Arg Cys Val Ala Ser Val Pro Ser Ile Pro Gly
                405                 410                 415
Leu Asn Arg Thr Gln Leu Val Lys Leu Ala Ile Phe Gly Pro Pro Trp
                420                 425                 430
Met Ala Phe Lys Glu Arg Lys Val Trp Val Lys Glu Asn Met Val Leu
            435                 440                 445
Asn Leu Ser Cys Glu Ala Ser Gly His Pro Arg Pro Thr Ile Ser Trp
450                 455                 460
```

-continued

```
Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
            485                 490                 495

Val Glu Cys Thr Ala Ser Asn Asp Leu Gly Lys Asn Thr Ser Ile Leu
        500                 505                 510

Phe Leu Glu Leu Val Asn Leu Thr Thr Leu Thr Pro Asp Ser Asn Thr
    515                 520                 525

Thr Thr Gly Leu Ser Thr Ser Thr Ala Ser Pro His Thr Arg Ala Asn
530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Thr Glu Leu
            595                 600                 605

Val Val Glu Val Lys Ser Asp Lys Leu Pro Glu Glu Met Gly Leu Leu
610                 615                 620

Gln Gly Ser Ser Gly Asp Lys Arg Ala Pro Gly Asp Gln Gly Glu Lys
625                 630                 635                 640

Tyr Ile Asp Leu Arg His
                645
```

<210> SEQ ID NO 5
<211> LENGTH: 1962
<212> TYPE: DNA
<213> ORGANISM: Artificial Sequence
<220> FEATURE:
<223> OTHER INFORMATION: Description of Artificial Sequence:HUMAN MUC18
      cDNA, AS MODIFIED TO FACILITATE CLONING

<400> SEQUENCE: 5

```
ctcggatcca tggggcttcc caggctggtc tgcgccttct tgctcgccgc ctgctgctgc      60
tgtcctcgcg tcgcgggtgt gcccggagag gctgagcagc ctgcgcctga gctggtggag     120
gtggaagtgg gcagcacagc ccttctgaag tgcggcctct cccagtccca aggcaacctc     180
agccatgtcg actggttttc tgtccacaag gagaagcgga cgctcatctt ccgtgtgcgc     240
cagggccagg gccagagcga acctggggag tacgagcagc ggctcagcct ccaggacaga     300 gggctactc tggccctgac tcaagtcacc ccccaagacg agcgcatctt cttgtgccag     360
ggcaagcgcc ctcggtccca ggagtaccgc atccagctcc gcgtctacaa agctccggag     420
gagccaaaca tccaggtcaa ccccctgggc atccctgtga acagtaagga gcctgaggag     480
gtcgctacct gtgtagggag gaacgggtac cccattcctc aagtcatctg gtacaagaat     540
ggccggcctc tgaaggagga gaagaaccgg tccacattc agtcgtccca gactgtggag     600
tcgagtggtt tgtacacctt gcagagtatt ctgaaggcac agctggttaa agaagacaaa     660
gatgcccagt tttactgtga gctcaactac cggctgccca gtgggaacca catgaaggag     720
tccagggaag tcaccgtccc tgttttctac ccgacagaaa aagtgtggct ggaagtggag     780
cccgtgggaa tgctgaagga aggggaccgc gtggaaatca ggtgtttggc tgatggcaac     840
cctccaccac acttcagcat cagcaagcag aaccccagca ccaggaggc agaggaagag     900 acaaccaacg acaacggggt cctggtgctg agcctgcccg gaaggaaca cagtgggcgc     960
```

```
tatgaatgtc aggcctggaa cttggacacc atgatatcgc tgctgagtga accacaggaa    1020
ctactggtga actatgtgtc tgacgtccga gtgagtcccg cagcccctga gagacaggaa    1080
ggcagcagcc tcaccctgac ctgtgaggca gagagtagcc aggacctcga gttccagtgg    1140
ctgagagaag agacagacca ggtgctggaa aggggggcctg tgcttcagtt gcatgacctg   1200
aaacgggagg caggaggcgg ctatcgctgc gtggcgtctg tgcccagcat acccggcctg    1260
aaccgcacac agctggtcaa gctggccatt tttggccccc cttggatggc attcaaggag    1320
aggaaggtgt gggtgaaaga gaatatggtg ttgaatctgt cttgtgaagc gtcagggcac    1380
ccccggccca ccatctcctg gaacgtcaac ggcacggcaa gtgaacaaga ccaagatcca    1440
cagcgagtcc tgagcaccct gaatgtcctc gtgaccccgg agctgttgga dacaggtgtt    1500
gaatgcacgg cctccaacga cctgggcaaa aacaccagca tcctcttcct ggagctggtc    1560
aatttaacca ccctcacacc agactccaac acaaccactg gcctcagcac ttccactgcc    1620
agtcctcata ccagagccaa cagcacctcc acagagagaa agctgccgga gccggagagc    1680
cggggcgtgg tcatcgtggc tgtgattgtg tgcatcctgg tcctggcggt gctgggcgct    1740
gtcctctatt tcctctataa gaagggcaag ctgccgtgca ggcgctcagg gaagcaggag    1800
atcacgctgc ccccgtctcg taagaccgaa cttgtagttg aagttaagtc agataagctc    1860
ccagaagaga tgggcctcct gcagggcagc agcggtgaca gagggctcc gggagaccag    1920 ggagagaaat acatcgatct gaaggcatta gccccgaatc at                      1962
```

<210> SEQ ID NO 6
<211> LENGTH: 28
<212> TYPE: DNA
<213> ORGANISM: Artificial Sequence
<220> FEATURE:
<223> OTHER INFORMATION: Description of Artificial
      Sequence:OLIGONUCLEOTIDE, FOR SUBCLONING HUMAN
      MUC18 FRAGMENT

<400> SEQUENCE: 6
ggatcccagc tggttaaaga agacaaag                                      28

<210> SEQ ID NO 7
<211> LENGTH: 27
<212> TYPE: DNA
<213> ORGANISM: Artificial Sequence
<220> FEATURE:
<223> OTHER INFORMATION: Description of Artificial
      Sequence:OLIGONUCLEOTIDE, FOR SUBCLONING HUMAN
      MUC18

<400> SEQUENCE: 7
ctggaactcg aggtcctggc tactctc                                       27

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:AMINO ACID
      SEQUENCE ENCODED BY PORTION OF PGEX-6P-1 VECTOR

<400> SEQUENCE: 8

Gly Pro Leu Gly Ser
 1               5

<210> SEQ ID NO 9

```
<211> LENGTH: 27
<212> TYPE: DNA
<213> ORGANISM: Artificial Sequence
<220> FEATURE:
<223> OTHER INFORMATION: Description of Artificial
      Sequence:OLIGONUCLEOTIDE, SEQUENCE CORRESPONDS TO
      HUMAN MUC18

<400> SEQUENCE: 9
ctcgggatcc atgggcttc ccaggct                                            27

<210> SEQ ID NO 10
<211> LENGTH: 25
<212> TYPE: DNA
<213> ORGANISM: Artificial Sequence
<220> FEATURE:
<223> OTHER INFORMATION: Description of Artificial
      Sequence:OLIGONUCLEOTIDE, SEQUENCE CORRESPONDS TO
      HUMAN MUC18

<400> SEQUENCE: 10
tcggggctaa tgcctcagat cgatg                                             25

<210> SEQ ID NO 11
<211> LENGTH: 81
<212> TYPE: DNA
<213> ORGANISM: Artificial Sequence
<220> FEATURE:
<223> OTHER INFORMATION: Description of Artificial Sequence:JUNCTION
      SEQUENCE FOR MCU18 CLONED INSERT

<400> SEQUENCE: 11
ctggaagttc tgttccaggg gccctgggga tccccggaat tcccgggtcg actcgagcgg        60
ccgcatcgtg actgactgac g                                                 81

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence:JUNCTION
      SEQUENCE FOR CLONED MUC18 INSERT

<400> SEQUENCE: 12

Leu Glu Val Leu Phe Gln Gly Pro Leu Gly Ser Pro Glu Phe Pro Gly
  1               5                  10                  15

Arg Leu Glu Arg Pro His Arg Asp
            20

<210> SEQ ID NO 13
<211> LENGTH: 81
<212> TYPE: DNA
<213> ORGANISM: Artificial Sequence
<220> FEATURE:
<223> OTHER INFORMATION: Description of Artificial Sequence:JUNCTION
      SEQUENCE FOR CLONED MUC18 INSERT

<400> SEQUENCE: 13
ctggaagttc tgttccaggg gccctgggga tccccaggaa ttcccgggtc gactcgagcg        60
gccgcatcgt gactgactga c                                                 81

<210> SEQ ID NO 14
<211> LENGTH: 23
<212> TYPE: PRT
<213> ORGANISM: Artificial Sequence
<220> FEATURE:
```

```
-continued

<223> OTHER INFORMATION: Description of Artificial Sequence:JUNCTION
      SEQUENCE IN FUSION PROTEIN

<400> SEQUENCE: 14

Leu Glu Val Leu Phe Gln Gly Pro Leu Gly Ser Pro Gly Ile Pro Gly
  1               5                  10                  15

Ser Thr Arg Ala Ala Ala Ser
             20

<210> SEQ ID NO 15
<211> LENGTH: 78
<212> TYPE: DNA
<213> ORGANISM: Artificial Sequence
<220> FEATURE:
<223> OTHER INFORMATION: Description of Artificial Sequence:JUNCTION
      SEQUENCE IN VECTOR WITH MCU18 CLONED INSERT

<400> SEQUENCE: 15
ctggaagttc tgttccaggg gcccctggga tccccgaatt cccgggtcga ctcgagcggc      60
cgcatcgtga ctgactga                                                   78

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence:JUNCTION OF
      FUSION PEPTIDE

<400> SEQUENCE: 16

Leu Gly Val Leu Phe Gln Gly Pro Leu Gly Ser Pro Asn Ser Arg Val
  1               5                  10                  15

Asp Ser Ser Gly Arg Ile Val Thr Asp
             20                  25
```

DIAGNOSTIC FOR METASTATIC PROSTATE CANCER

CROSS REFERENCE TO RELATED APPLICATIONS

This application is a continuation of International Application PCT US99/04850, filed Mar. 2, 1999 and designating the Unites States, which application claims priority from U.S. Provisional Application No. 60/076,664 filed Mar. 3, 1998.

ACKNOWLEDGMENT OF FEDERAL RESEARCH SUPPORT

Not applicable.

BACKGROUND OF THE INVENTION

Prostate cancer accounts for about 1 in 10 cancer cases in the United States, and it is the most often diagnosed cancer in males [Henderson et al. (1991) Science 254,1131–1138]. While in many affected patients, the tumors are slow-growing and nonmetastatic, in others the malignant prostate tumors are aggressive and metastasize. When prostate cancer metastasizes, the prognosis for the patient is poor, especially without treatment.

To date, the most frequently used test for prostate cancer is the serum level of prostate specific antigen (PSA) and the radionuclide bone scan for detecting prostate cancer metastases before definitive therapy is initiated. However, the elevated level of PSA in serum is not predictive of the pathologic stage of the prostate cancer or the presence of metastatic disease. PSA, a serine protease, is not exclusively expressed in the epithelial cells of metastatic prostate cancer, but it is also expressed in normal epithelial cells, primary tumors and benign prostate hyperplasia.

The altered expression of cell-adhesion molecules has been correlated with metastasis of many cancers. Low or no expression of E-cadherin, a cell-adhesion molecule, has been found in high-grade prostate carcinoma, and this indicates a poor prognosis for those prostate cancer patients. However, the absence of an antigen is not very useful as a diagnostic marker for cancer metastasis.

MUC18 is a glycoprotein of about 113 kDa which serves as a cell adhesion molecule on the surface of melanoma cells, and it has been correlated with the ability of melanomas to metastasize [See, e.g., Lehmann et al. (1989) Proc. Nat. Acad. Sci. USA 86, 9891–9895; Luca et al. (1993) Melanoma Res. 3, 3541; Johnson et al. (1996) Curr. Top. Microbiol. Immunol. 213, 95–105; Xie et al. (1997) Cancer Res. 57, 2295–2303; Tang and Honn (1994–1995) Invasion Metas. 14, 109–122; Rummel et al. (1996) Cancer Res. 56, 2218–2223]. MUC18 is also known as MCAM and CD146. MUC18 carries a carbohydrate modification known as HNK-1 or CD57 [Shih et al. (1994) Cancer Res. 54, 2514–2520]. Besides being associated with melanoma cells' ability to metastasize, MUC18 is also associated with normal vascular tissue, and on the smooth muscle of venules, and it expresses sporadically on capillary epithelium [Johnson, J. (1994–1995) Invasion Metas. 14, 123–130].

There is a longfelt need in the art for an improved diagnostic test for metastatic prostate cancer so that appropriate therapy can be initiated as soon as possible and so that the number of false positive results can be minimized.

SUMMARY OF THE INVENTION

The present invention provides an improved diagnostic test for prostate cancer which has a relatively high potential for metastasis or which has metastasized. This allows the physician to choose appropriate surgical, chemotherapeutic or radiation treatment regimens. This improved assay is based on the correlation of high levels of expression of the MUC18 coding sequence as measured by MUC18 mRNA or MUC18 protein. This expression can be detected at the transcriptional level, where mRNA levels are monitored, or detection of the MUC18 gene product at the translation level can be determnined, for example, through the use of an immunoassay for the MUC18 protein. The source of the material for these tests is prostate biopsy tumor tissue (e.g., from a needle biopsy) from a patient needing a determination of the metastatic potential of a prostate tumor or from cells from a prostate tumor.

Relative levels of transcriptional expression (mRNA) of the MUC18 coding sequence can be determined by Northern hybridization analysis or by quantitative reverse transcription polymerase chain reaction (RT-PCR) in normal and neoplastic prostate tissue samples and in biopsy material.

Translational expression of MUC18 can be determined by any of a number of adaptations of an immunoassay using antibody specific for the MUC18 cell surface antigen. The relative level of MUC18 can be determined by standard immunoassays using a MUC18-specific antibody preparation and a detection system suitable for the assay. Immunoassays can include, but are not limited to, immunofluorescence assays, radioimmunoassay, enzyme-linked immunosorbent assays, and Western (immuno) blot assays. In the context of the present invention, relative amounts of the MUC18 protein are determined in tissue samples (e.g., biopsy material).

It is a further object of the present invention to provide an antibody which inhibits prostate cancer metastasis. In particular, antibody specific to MUC18 prevents metastasis of prostate cancer cells.

Additional objects include vectors directing the expression of an immunogenic fragment of human MC18and the corresponding recombinantly expressed protein. As specifically exemplified, an immunogenic fragment of human MUC18 is encoded by the PvuII to XhoI fragment within the sequence given in Tables 1A–1B.

BRIEF DESCRIPTION OF THE DRAWINGS

FIG. 1 shows the results for RT-PCR amplified human MUC18 cDNA (left panel) and cloning of the whole cDNA and its fragments into a GST-fusion protein expression vector (right panel). RT-PCR amplification of human MUC18 cDNA from the poly(A)+RNA isolated and purified from a human melanoma cell line, Sk-Mel-28. Left panel: Lane (a) shows the expected PCR product of 1957 bp (as indicated by an arrow head). Lane (ml) shows the 1 kb ladders and lane (m2) the 123-bp ladders as DNA molecular size markers. Right panel: The plasmid map of the cloned whole human MUC18 cDNA and three fragments in a GST-fusion expression system.

FIG. 3 depicts recombinant human MUC18-middle fragment. The plasmid map is shown in FIG. 1. The left panel shows the PAGE result and right panel the Superdex column purification. The GST-human MUC18 middle fragment fusion protein is shown after IPTG induction (a & b, indicated by a triangle on the left of the left panel). The fusion protein was first purified through a glutathione-Sepharose affinity column and then cleaved with the HRV-3C protease (left panel, lanes c–e). The affinity-purified recombinant human MUC18-middle fragment was then further purified through a Superdex column (right panel) to remove high molecular weight contaminants (peaks I and II, fractions 3–13). The final recombinant human MUC18-middle fragment protein is about 22 kDa (peak III, fractions 14–20), as indicated by a triangle on the right in the left panel.

DETAILED DESCRIPTION OF THE INVENTION

Figure 2:
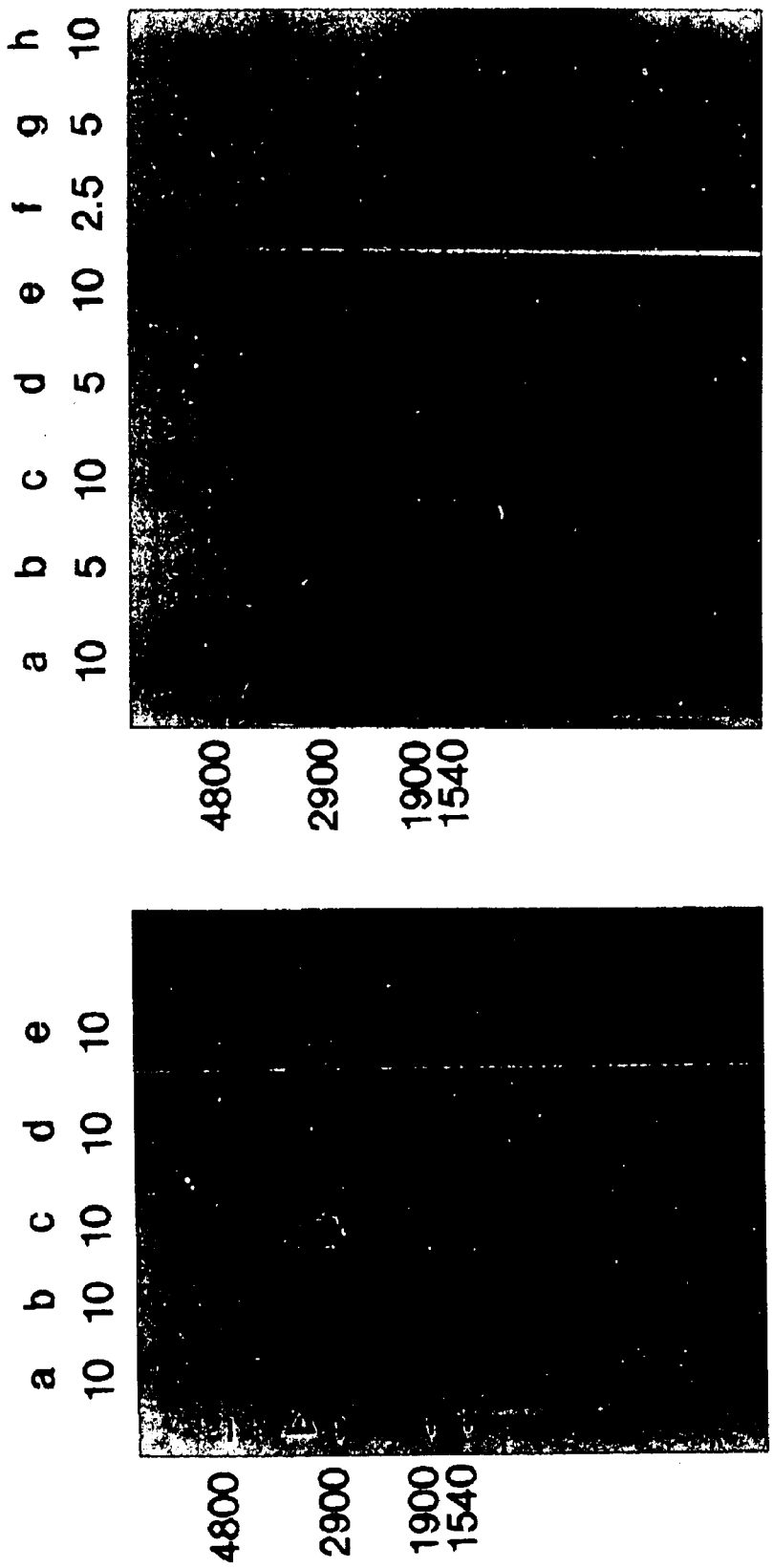
FIGS. 2A and 2B illustrate Northern blot analysis of expression of human MUC18 in different prostate cancer cell lines. Poly(A)$^+$RNA was isolated from human melanoma cells SK-MEL-28 (SK), human melanocyte (M), and human prostate cancer cells PC-3 (PC-3), DU145 (DU), TSU-PR-1 (TSUPR1), and LNCAP (LNCAP). The size of the human MUC18 mRNA is 3.3 kb. The amount of poly (A)$^+$ RNA (2.5 to 10 µg) is indicated as a number on top of each lane.
Figure 4:
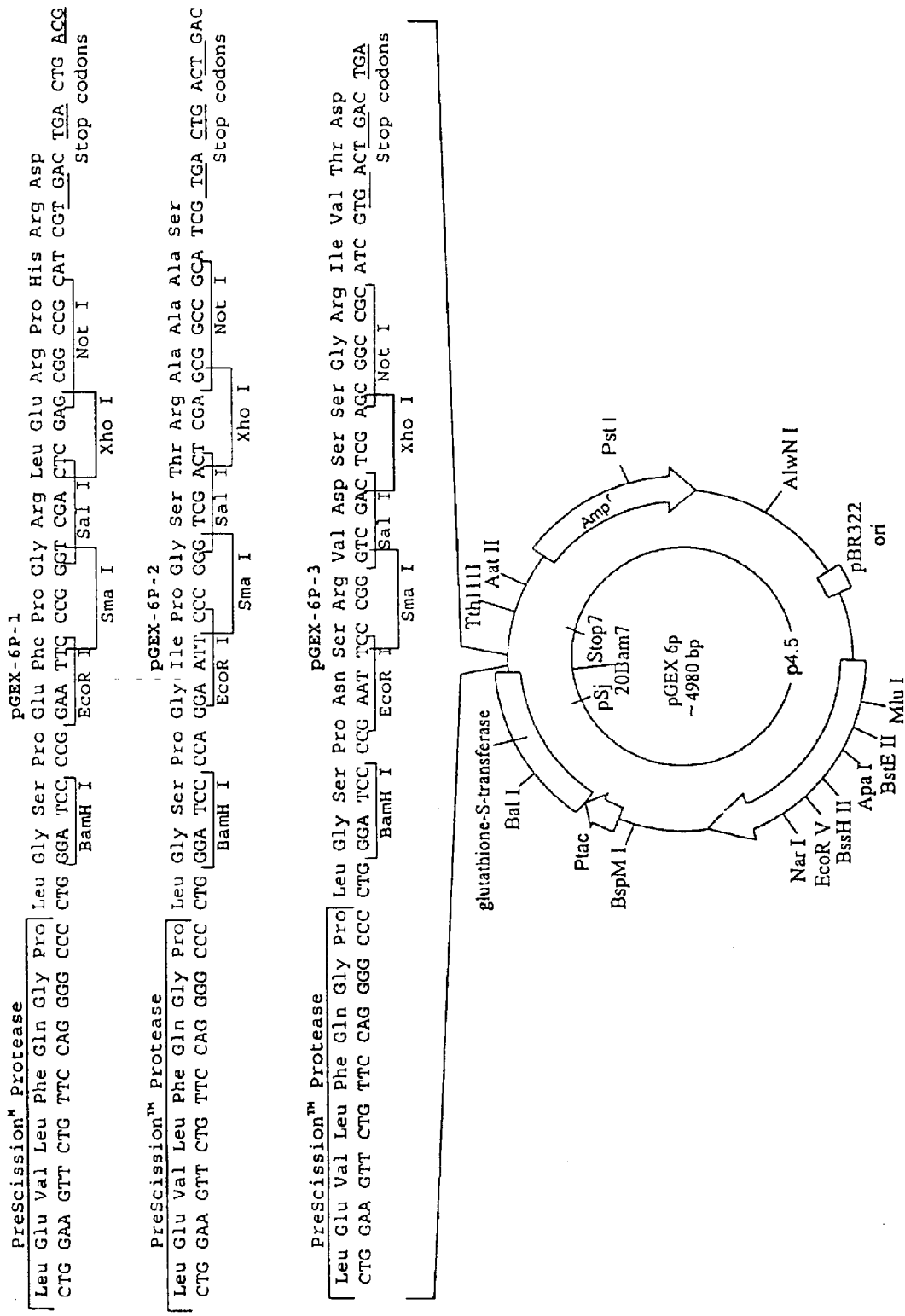
FIG. 4 shows pGEX-6P, commercially available from Pharmacia Biotech, Piscataway, N.J. The specific multiple cloning site (MCS) sequences for pGEX-6P-1 (SEQ ID NO:11, encoded amino acids, SEQ ID NO:12), pGEX-6P-2 (SEQ ID NO:13, encoded amino acids, SEQ ID NO:14 and pGEX-6P-3 (SEQ ID NO:15, encoded amino acids, SEQ ID NO:16) are provided.

Prostate cancer accounts for about 10% of all cancer cases in the United States. It is now the most frequently diagnosed cancer in American males [Rinker-Schaeffer et al. (1993) *Cancer and Metas. Rev*12, 3–10]. In some patients prostate cancers metastasize rapidly, killing the patient within one year of the initial clinical presentation. In contrast, some other prostate cancer patients show a relatively slow growth of the malignant tumor without metastasis. The majority of the histologically localized prostate cancers remain subclinical and never require treatment. Prostate cancer, when truly localized, can be cured by radical prostatectomy. While in many affected patients, the tumors are slow-growing and nomnetastatic, in others prostate cancer takes a more aggressive course. Unfortunately, metastatic prostate cancer is a fatal disease without treatment.

At present, the test for serum levels of prostate specific antigen (PSA) and the radionuclide bone scan are the only diagnostic tests available before therapy is initiated. However, an elevated level of PSA observed in serum is not predictive of the pathological state of prostate cancer, nor is it correlated with metastatic prostate cancer. This is, at least in part, because PSA, a serine protease, is not exclusively expressed in the epithelial cells of metastatic prostate cancer, but it is also expressed in normal epithelial cells, primary prostate cancerous tumors and benign prostatic hyperplasia [Wood et al. (1994) *Cancer* 74, 2533–2540]. To date, it has not been possible to predict whether histologically detected localized tumors are likely to progress to clinical cancer or when these localized tumors are likely to metastasize to other sites within the body. Thus, there is an urgent need for biochemical markers which serve to identify prostate cancers which have progressed to a stage which requires immediate surgical removal and/or additional chemotherapeutic or radiation therapeutic treatments, i.e., those cancers which are likely to metastasize.

To identify a diagnostic marker which is improved over PSA, it is crucial to understand the biochemical differences between the malignant state and the benign state and between tumor cells with high and low metastatic potential. Overexpression and underexpression of certain cell adhesion molecules at the cell surface has been proposed to reflect metastasis of several cancers [Tang and Honn (1994–1995) *Invasion Metas*. 14, 109–122]. For example, the low expression of E-cadherin has been correlated with poor prognosis of prostate cancer [Rinker-Schaeffer et al. (1993) supra]. The present invention provides a positive correlation between the level of MUC18 expression and high metastatic potential of prostate cancer cells.

The human MUC18 (huMUC18) cDNA sequence (see Table 1A) obtained by the present inventors is different from the huMUC18 cDNA sequence given in GenBank Accession No. N28882 [Johnson et al. (1994)]. The deduced amino acid sequence of huMUC18 cDNA given in Table 1A was identical to the huMUC18 sequence deposited in GenBank by Johnson's group except seven amino acid residues. This discrepancy of amino acid sequence may be due to allelic differences. However, the amino acid sequence of the inventor's huMUC18 (646 amino acids) was very different from that published by Johnson's group in 1989 (603 amino acids), which 1989 sequence appears to contain sequence errors in the huMUC18 cDNA.

The human MUC18 cDNA sequence disclosed in Table 1A was amplified by RT-PCR from poly(A)+RNA, which was isolated from the human melanoma cell line SK-Mel-28. The cDNA was cloned into the pGEM-T-easy vector (Promega, Madison, Wis.). The DNA sequence of the huMUC18 cDNA was determnined by rapid DNA sequencing using ABI prism dye terminator cycle sequencing ready reaction kit (Perkin-Elmer) with various huMUC18 specific primers in an automated sequencer of ABI 373XL system. The Lasergen and GCG programs were used for comparison of nucleotide and amino acid sequences of the huMUC18 cDNA.

A cDNA sequence of a human MUC18 clone has been published in GenBank™ under Accession No. M 28882 (See Table 1B). The translation initiation codon (ATG) is underlined, as is the translation termination codon (TAG). The PvuII (CAGCTG) and XhoI (CTCGAG) restriction sites are boxed, and cut sites are indicated by vertical arrows.

Table 1C (see also SEQ ID NO:5) shows the human MUC18 sequence as modified to introduce a BamHI site (GGATCC) just upstream of the translation start site to facilitate cloning. The translation initiation (ATG) and termination (TAG) codons are boxed. The long arrows near the 5' and

TABLE 1A

HUMAN MUC18 cDNA SEQUENCE WITH DEDUCED AMINO ACID SEQUENCE

```
   1  ATG GGG CTT CCC AGG CTG GTC TGC CTC TTG GCC GCC GTC GCG GGT CCT GTG CCC GGA GAG GCT GTC AGC CAT GTC      90
      Met Gly Leu Pro Arg Leu Val Cys Leu Leu Ala Ala Val Ala Gly Pro Val Pro Gly Glu Ala Val Ser His Val

91  CCT GCG CCT GAG CTG GTG GAG AAG GTG ACA ACA TGC AAG CTT GTG CTC CGG CGC TCC TCC CAG GGC AAC CTC TCC     180
      Pro Ala Pro Glu Leu Val Glu Lys Val Thr Thr Cys Lys Leu Val Leu Arg Cys Ser Ser Gln Gly Asn Leu Ser

181  GAC TGG TTT TCT GTC CAC TGG AGT CAG CTC ACG CTC ATC ATC TTC CGT GTG CAG GGC GAA CCT GGG GAG TAC GAG GAG     270
      Asp Trp Phe Ser Val His Trp Ser Gln Leu Thr Leu Ile Ile Phe Arg Val Gln Gly Glu Pro Gly Glu Tyr Glu Gln

271  CGG CTC AGC CTC CAG GAG CTC CAG AGA GGG GCT ACT CTG CAA GTC GCC CAC ATC TTT CGC CAG GGC AAG CGC     360
      Arg Leu Ser Leu Gln Glu Leu Gln Arg Gly Ala Thr Leu Gln Val Ala His Ile Phe Arg Gln Gly Lys Arg

361  CCT CGG AGT TCC CAG GAG TAC GAG CTC CGC ATC TAC AAA GCT GTC CCG GAG CCA ATC CTG GGC ATC CCT GTG     450
      Pro Arg Ser Ser Gln Glu Tyr Glu Leu Arg Ile Tyr Lys Ala Val Pro Glu Pro Ile Leu Gly Ile Pro Val

451  AAC AGT AAG AAG CCT GCT GTC TAC CTG GTA GTG TAC AAA AAC CCT CCC ATT CAA GTC ATC TGG TAC AAT GGC CGG CCT     540
      Asn Ser Lys Lys Pro Ala Val Ala Thr Cys Val Val Tyr Asn Gly Arg Tyr Pro Ile Gln Val Ile Trp Tyr Asn Gly Arg Pro

541  CTG AAG GAG GAG AAC GGG GTC CAC ATT CAG GAG TCG AGT TCC ACT TTG TAC ACC CTG AGT AGT ATT CTG AAG GCA     630
      Leu Lys Glu Glu Asn Gly Val His Ile Gln Glu Ser Ser Thr Leu Tyr Thr Leu Ser Ser Ile Leu Lys Ala

631  CAG GTG GTT AAA GAA GAT GCC CAG CAG TTT TAC TGC CTC CTC AAC TAC CCG CTC CTG TAC CAG AAC CAC ATG GAG TCC AGG GAA     720
      Gln Val Val Lys Glu Asp Ala Gln Gln Phe Tyr Cys Leu Leu Asn Tyr Arg Leu Pro Ser Gly Asn His Met Lys Ser Arg Glu

721  GTC ACC GTC CCT GTT TTC TAC CCC ACA GAA GTG GTG CTG GGA ATG AAG CTG GGT GAT CGC GTG GAA ATC     810
      Val Thr Val Pro Val Phe Tyr Pro Thr Glu Val Val Leu Gly Met Lys Leu Gly Asp Arg Val Glu Ile

811  AGG TGT TTG GCT GAT GGC AAC CCT CCA CCA CAT TTC TCC AGC ATC AGC TGG AAC AGG GAG GCA GAA GAG ACA GGC ACA AAC     900
      Arg Cys Leu Ala Asp Gly Asn Pro Pro Pro His Phe Ser Ile Ser Trp Arg Gln Asn Pro Ser Thr Arg Glu Ala Glu Glu Thr Asn

901  GAC AAC GGG GTC CTG GTG CTG GAA CCA GCT CGG AAG GAA CAC AGT GGG CGC TAT GTG TGT CGA GCC CAT GAA     990
      Asp Asn Gly Val Leu Val Leu Glu Pro Ala Arg Lys Glu His Ser Gly Arg Tyr Val Cys Arg Ala His Glu

991  CTC CTG GAA GTC CTG CTG GTG CTG CTG GTC GAC TAT GTG GAA TCC AGT CCC GCA GCC CCT GAG AGA CAG GAA GGC AGC     1080
      Leu Leu Glu Val Leu Leu Val Leu Leu Val Asp Tyr Val Glu Ser Ser Pro Ala Ala Pro Glu Arg Gln Glu Gly Ser Ser

1081  CTC ACC CTG ACC TGT GAG GCA GAG AGT AGT CAG GAT CTG TAC TGG AGA GAG ACA GGC GTG GAA AGG GGG CCT     1170
      Leu Thr Leu Thr Cys Glu Ala Glu Ser Ser Gln Asp Leu Tyr Trp Arg Glu Thr Gly Val Glu Arg Gly Pro

1171  GTG CTT CAG TTG CAT CTC CAT GAG CAG AGT CTG AAG CCG GCA GCA GAA TGC TGC GGC TAT GTG TCT GTG GCG GTG     1260
      Val Leu Gln Leu His Leu His Glu Gln Ser Leu Lys Pro Ala Ala Glu Cys Cys Gly Tyr Val Ser Val Ala

1261  CAG CTT GAA CTC GGG CGC ATT TTT GGC AAG CTG CCC CGG AAA AGG GAG CTG TGG GTG AAG GAG GTG TCT GTG TGG AAT ATG     1350
      Gln Leu Glu Leu Gly Arg Ile Phe Gly Lys Leu Pro Arg Lys Arg Glu Leu Trp Val Lys Glu Val Ser Val Trp Asn Met

1351  TCT TGT GAA GGG TCA GGG CAC CCC CGG AGG GAG GTC GTG GAA GTA GTT GCA AAC GTC ACG GGC CAA AGT CAG CGA GTC     1440
      Ser Cys Glu Gly Ser Gly His Pro Arg Arg Glu Val Val Glu Val Val Ala Asn Val Thr Gly Gln Ser Gln Arg Val

1441  CTG ACC AGC CTG AAT GTC CTC GAG ACC CCG GAG GAG CTG TTG GAC ACA GGG CTT GAG AGC TGC GTT GAA CCA TTC ACG AAA AAC AGC     1530
      Leu Thr Ser Leu Asn Val Leu Glu Thr Pro Glu Glu Leu Leu Asp Thr Gly Leu Glu Ser Cys Val Glu Pro Phe Thr Lys Asn Ser
```

TABLE 1A-continued

HUMAN MUC18 cDNA SEQUENCE WITH DEDUCED AMINO ACID SEQUENCE

```
       Leu Ser Thr Leu Asn Val Leu Val Thr Pro Glu Leu Leu Glu Thr Gly Val Glu Cys Thr Ala Ser Asn Asp Leu Gly Lys Asn Thr Ser
1531   ATC CTC TTC GAG CTG GTC AAT TTA ACC ACC CTC ACA GAC TCC AAC ACA ACC ACT GGC CTC AGC ACT GCC AGT CCT GAT          1620
       Ile Leu Phe Glu Leu Val Asn Leu Thr Thr Leu Thr Asp Ser Asn Thr Thr Gly Leu Ser Thr Ala Ser Pro His
1621   ACC AGA GGC AAC ACC TCC ACA GAG AAG AGA GAG CTG CCG GAG AGC CGG GTG GCT GTG ATT GTG TGC ATC CTG          1710
       Thr Arg Ala Asn Thr Ser Thr Glu Lys Arg Glu Leu Pro Glu Ser Arg Val Ala Val Ile Val Cys Ile Leu
1711   GTC CTG GCG GTG CTG GGC GCT GTC CTC TAT TTC CTC TAC AAG GGC TCA AGG CGC AAG CAG GAG ATC AGG AGG CTG          1800
       Val Leu Ala Val Leu Gly Ala Val Leu Tyr Phe Leu Tyr Lys Gly Ser Arg Arg Lys Gln Glu Ile Thr Leu
1801   CGC CGG TCT AAG AGC GAA CTT GTA GTT GAA GTT TCA GAT AAG CTC CCA GAA GAG ATG GCC CTG CAG GGC AGC GGT GAC          1890
       Pro Ser Arg Lys Ser Glu Leu Val Val Glu Val Ser Asp Lys Leu Pro Glu Glu Met Gly Leu Leu Gln Gly Ser Ser Gly Asp
1891   AAG AGG GCT CGG CCA GAC CAG CAG GGA GAG AAA TAG GAT CTG AGG CAT TAG CCCCGAAAT
       Lys Arg Ala Arg Pro Asp Gln Gln Gly Glu Lys Tyr Ile Asp Leu Arg His End
```

TABLE 1B

HUMAN MUC18 cDNA (GENBANK ACCESSION NO. M28882).

GGGAAGCATGGGGCTTCCCAGGCTGGTCTGCGCCTTCTTGCTCGCCGCCTGCTGCTGCTGTCCTCGCGTC

GCGGGTGTGCCCGGAGAGGCTGAGCAGCCTGCGCCTGAGCTGGTGGAGGTGGAAGTGGGCAGCACAGCCC

TTCTGAAGTGCGGCCTCTCCCAGTCCCAAGGCAACCTCAGCCATGTCGACTGGTTTTCTGTCCACAAGGA

GAAGCGGACGCTCATCTTCCGTGTGCGCCAGGGCCAGGGCCAGAGCGAACCTGGGGAGTACGAGCAGCGG

CTCAGCCTCCAGGACAGAGGGGCTACTCTGGCCCTGACTCAAGTCACCCCCCAAGACGAGCGCATCTTCT

TGTGCCAGGGCAAGCGCCCTCGGTCCCAGGAGTACCGCATCCAGCTCCGCGTCTACAAAGCTCCGGAGGA

GCCAAACATCCAGGTCAACCCCCTGGGCATCCCTGTGAACAGTAAGGAGCCTGAGGAGGTCGCTACCTGT

GTAGGGAGGAACGGGTACCCCATTCCTCAAGTCATCTGGTACAAGAATGGCCGGCCTCTGAAGGAGGAGA

AGAACCGGGTCCACATTCAGTCGTCCCAGACTGTGGAGTCGAGTGGTTTGTACACCTTGCAGAGTATTCT

GAAGGCACAGCTGGTTAAAGAAGACAAAGATGCCCAGTTTTACTGTGAGCTCAACTACCGGCTGCCCAGT

GGGAACCACATGAAGGAGTCCAGGGAAGTCACCGTCCCTGTTTTCTACCCGACAGAAAAAGTGTGGCTGG

AAGTGGAGCCCGTGGGAATGCTGAAGGAAGGGGACCGCGTGGAAATCAGGTGTTTGGCTGATGGCAACCC

TCCACCACACTTCAGCATCAGCAAGCAGAACCCCAGCACCAGGGAGGCAGAGGAAGAGACAACCAACGAC

AACGGGGTCCTGGTGCTGGAGCCTGCCCGGAAGGAACACAGTGGGCGCTATGAATGTCAGGCCTGGAACT

TGGACACCATGATATCGCTGCTGAGTGAACCACAGGAACTACTGGTGAACTATGTGTCTGACGTCCGAGT

GAGTCCCGCAGCCCCTGAGAGACAGGAAGGCAGCAGCCTCACCCTGACCTGTGAGGCAGAGAGTAGCCAG

GACCTCGAGTTCCAGTGGCTGAGAGAAGAGACAGACCAGGTGCTGGAAAGGGGGCCTGTGCTTCAGTTGC

ATGACCTGAAACGGGAGGCAGGAGGCGGCTATCGCTGCGTGGCGTCTGTGCCCAGCATACCCGGCCTGAA

CCGCACACAGCTGGTCAAGCTGGCCATTTTTGGCCCCCCTTGGATGGCATTCAAGGAGAGGAAGGTGTGG

GTGAAAGAGAATATGGTGTTGAATCTGTCTTGTGAAGCGTCAGGGCACCCCGGCCCACCATCTCCTGGA

ACGTCAACGGCACGGCAAGTGAACAAGACCAAGATCCACAGCGAGTCCTGAGCACCCTGAATGTCCTCGT

GACCCCGGAGCTGTTGGAGACAGGTGTTGAATGCACGGCCTCCAACGACCTGGGCAAAAACACCAGCATC

CTCTTCCTGGAGCTGGTCAATTTAACCACCCTCACACCAGACTCCAACACAACCACTGGCCTCAGCACTT

CCACTGCCAGTCCTCATACCAGAGCCAACAGCACCTCCACAGAGAGAAAGCTGCCGGAGCCGGAGAGCCG

GGGCGTGGTCATCGTGGCTGTGATTGTGTGCATCCTGGTCCTGGCGGTGCTGGGCGCTGTCCTCTATTTC

CTCTATAAGAAGGGCAAGCTGCCGTGCAGGCGCTCAGGGAAGCAGGAGATCACGCTGCCCCCGTCTCGTA

AGACCGAACTTGTAGTTGAAGTTAAGTCAGATAAGCTCCCAGAAGAGATGGGCCTCCTGCAGGGCAGCAG

CGGTGACAAGAGGGCTCCGGGAGACCAGGGAGAGAAATACATCGATCTGAGGCATTAGCCCCGAATCACT

TABLE 1C

HUMAN MUC18 cDNA WITH 5' MODIFICATION TO FACILITATE CLONING

```
 BamHI
BFI        ATGGGGCTTCCCAGGCTGGTCTGCGCCTTCTTGCTCGCCGCCTGCTGCTGCTGTCCTCGCGTC

GCGGGTGTGCCCGGAGAGGCTGAGCAGCCTGCGCCTGAGCTGGTGGAGGTGGAAGTGGGCAGCACAGCCC

TTCTGAAGTGCGGCCTCTCCCAGTCCCAAGGCAACCTCAGCCATGTCGACTGGTTTTCTGTCCACAAGGA

GAAGCGGACGCTCATCTTCCGTGTGCGCCAGGGCCAGGGCCAGAGCGAACCTGGGGAGTACGAGCAGCGG

CTCAGCCTCCAGGACAGAGGGGCTACTCTGGCCCTGACTCAAGTCACCCCCCAAGACGAGCGCATCTTCT

TGTGCCAGGGCAAGCGCCCTCGGTCCCAGGAGTACCGCATCCAGCTCCGCGTCTACAAAGCTCCGGAGGA

GCCAAACATCCAGGTCAACCCCCTGGGCATCCCTGTGAACAGTAAGGAGCCTGAGGAGGTCGCTACCTGT
```

TABLE 1C-continued

HUMAN MUC18 cDNA WITH 5' MODIFICATION TO FACILITATE CLONING

```
GTAGGGAGGAACGGGTACCCCATTCCTCAAGTCATCTGGTACAAGAATGGCCGGCCTCTGAAGGAGGAGA
AGAACCGGGTCCACATTCAGTCGTCCCAGACTGTGGAGTCGAGTGGTTTGTACACCTTGCAGAGTATTCT
GAAGGCACAGCTGGTTAAAGAAGACAAAGATGCCCAGTTTTACTGTGAGCTCAACTACCGGCTGCCCAGT
GGGAACCACATGAAGGAGTCCAGGGAAGTCACCGTCCCTGTTTTCTACCCGACAGAAAAAGTGTGGCTGG
AAGTGGAGCCCGTGGGAATGCTGAAGGAAGGGGACCGCGTGGAAATCAGGTGTTTGGCTGATGGCAACCC
TCCACCACACTTCAGCATCAGCAAGCAGAACCCCAGCACCAGGGAGGCAGAGGAAGAGACAACCAACGAC
AACGGGTCCTGGTGCTGGAGCCTGCCCGGAAGGAACACAGTGGGCGCTATGAATGTCAGGCCTGGAACT
TGGACACCATGATATCGCTGCTGAGTGAACCACAGGAACTACTGGTGAACTATGTGTCTGACGTCCGAGT
GAGTCCCGCAGCCCTGAGAGACAGGAAGGCAGCAGCCTCACCCTGACCTGTGAGGCAGAGAGTAGCCAG
GACCTCGAGTTCCAGTGGCTGAGAGAAGAGACAGACCAGGTGCTGGAAAGGGGGCCTGTGCTTCAGTTGC
ATGACCTGAAACGGGAGGCAGGAGGCGGCTATCGCTGCGTGGCGTCTGTGCCCAGCATACCCGGCCTGAA
CCGCACACAGCTGGTCAAGCTGGCCATTTTTGGCCCCCCTTGGATGGCATTCAAGGAGAGGAAGGTGTGG
GTGAAAGAGAATATGGTGTTGAATCTGTCTTGTGAAGCGTCAGGGCACCCCCGGCCCACCATCTCCTGGA
ACGTCAACGGCACGGCAAGTGAACAAGACCAAGATCCACAGCGAGTCCTGAGCACCCTGAATGTCCTCGT
GACCCCGGAGCTGTTGGAGACAGGTGTTGAATGCACGGCCTCCAACGACCTGGGCAAAAACACCAGCATC
CTCTTCCTGGAGCTGGTCAATTTAACCACCCTCACACCAGACTCCAACACAACCACTGGCCTCAGCACTT
CCACTGCCAGTCCTCATACCAGAGCCAACAGCACCTCCACAGAGAGAAAGCTGCCGGAGCCGGAGAGCCG
GGGCGTGGTCATCGTGGCTGTGATTGTGTGCATCCTGGTCCTGGCGGTGCTGGGCGCTGTCCTCTATTTC
CTCTATAAGAAGGGCAAGCTGCCGTGCAGGCGCTCAGGGAAGCAGGAGATCACGCTGCCCCCGTCTCGTA
AGACCGAACTTGTAGTTGAAGTTAAGTCAGATAAGCTCCCAGAAGAGATGGGCCTCCTGCAGGGCAGCAG
CGGTGACAAGAGGGCTCCGGGAGACCAGGGAGAGAAATACATCGATCTGAGGCATTAGCCCCGAATCACT
                                    ERGA
```

3' ends indicate primer positions (BF1 and ER6a, respectively). The cut site for BamHI within its recognition sequence (GGATCC) is indicated with a vertical arrow.

The GenBank™ 28882 sequence (given in SEQ ID NO:3) is identical to a human MUC18 cDNA clone (huMUC18) from human SK-Mel-28 cells, a human malignant melanoma cell line which produces relatively high levels of the MUC18 protein. This sequence is slightly different from the huMUC18 previously published [Johnson and Rummel (1996) in *Immunology of Human Melanoma*, ed, Maio, M., IOA Press, Washington, D.C., pp. 31–38; Lehmann et al. (1989) *Proc. Natl. Acad Sci. USA* 86, 9891–9895; Luca et al. (1993) *Melanoma Res.* 3, 35–41]. The two cDNAs have three stretches of amino acid (aa) residues that are different, such as 19 aa and 17 aa at the N-terminal portion and 17 aa near the C-terminal portion. Furthermore, the published human MUC18 cDNA sequence was missing 42 amino acids at the C-terminal end (see SEQ ID NO:4). The human and murine cDNAs have 74.5% identity in the deduced amino acid sequences. The 3'-end primer used previously, ER6, did not include the last few codons and the termination codon. To re-clone the intact correct human MUC18 cDNA, a correct new 3'-primer, ER6a, for amplifying the intact human MUC18 cDNA was designed (see hereinbelow).

Efforts to express the recombinant huMUC18 protein in the pCal-n expression system (Stratagene, La Jolla, Calif.) in *E. coli* failed. Finally, the expression was possible by using a GST-fusion protein expression system. The huMUC18 cDNA was cloned in the PGEX6p-1 vector (Pharmacia), a small amount of the nearly intact MUC18 protein in *E. coli* was expressed. Fortunately, the sequence of the middle portion of the huMUC18 cDNA was correct, and it was then used for making recombinant protein in *E. coli*. Only when the middle 166 amino acid portion encoded by the cDNA, but not the N-terminal or C-terminal portions, was used for expression, over-expression of the recombinant protein was possible. One pair of primers: BamHI-HMUC18-pvuII (28-mer, GGATCCCAGCTGGTTAAAGAAGACAAAG) (SEQ ID NO:6) and HMUC18-xhoI (27-mer, CTGGAACTCGAGGTCCTGGCTACTCTC) (SEQ ID NO:7) were used for PCR-amplification of the region from PvuII to XhoI of the HuMUC18 cDNA. The amplified fragment was cloned into pGEM-T Easy vector. The DNA fragment that included the coding region from the PvuII site to the XhoI site was excised from the pGEM-T Easy recombinant plasiid by two restriction enzymes, BamHI and SalI, and cloned into the BamHI and SalI cleaved pGEX-6P-1 vector. The recombinant HuMUC18-middle fragment after cleavage with PrScission protease and purification contained the following sequences (see also Table 1A and SEQ ID NO:2).

```
                  211                                            376
(Gly-Pro-Leu-Gly-Ser-)(SEQ ID NO:8)Gln-Leu-..........Leu-Glu-Phe-Gln-(Asn-His).
PGEX-6P-1 vector   (Amino acids 211-376 of SEQ ID NO:2)  pGEM T Easy vector
```

A 22 kDa protein fragment was expressed from the PvuII to XhoI fragment of the cDNA (see Tables 1A and 1C). A large-scale preparation of the recombinant human MUC18 "middle portion" fragment was carried out. More than 6 mg of the purified recombinant protein was obtained after purification through a glutathione-affinity column, cleavage with the HRV-3C protease, being eluted and concentrated, and further purification through a Superdex column in a Pharmacia FPLC system. After final concentration of the eluant, 6 mg of the "middle portion" recombinant protein was sent to Larnpire Biological Laboratories to make polyclonal antibodies in chickens. High antibody titers were reported. Eggs are collected and IgY (chicken antibody protein) is purified from these eggs. After the titers of these purified IgY preparations are determined, they are used for immunological testing.

Figure 6:
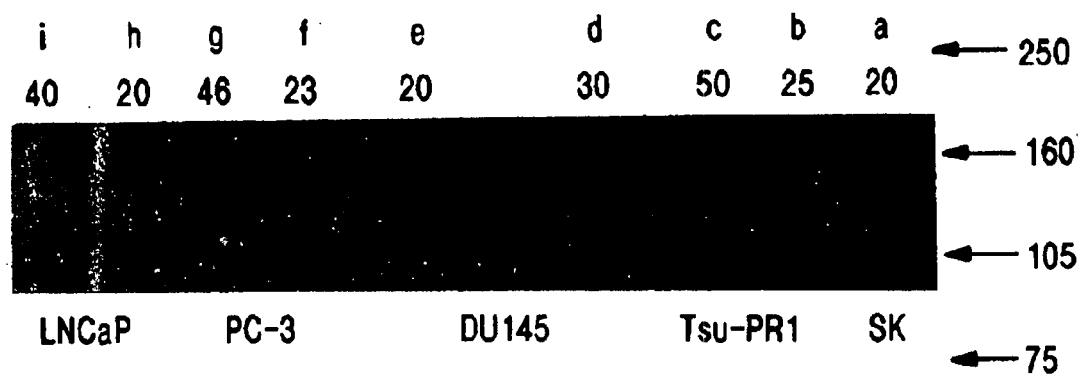
FIG. 6 illustrates the results of Western blot analysis of huMUC18 protein expression in four prostatic cancer cell lines. Cellular extracts of four prostatic cancer cell lines were prepared, and the proteins were size-separated by sodium dodecyl sulfate-polyacrylamide gel electrophoresis (SDS-PAGE). The anti-huMUC18 antibodies generated by immunization of the recombinant huMUC18-middle portion protein in chicken were used for Western blot analysis. SK stands for cellular lysate prepared from human SK-Mel-28 cells (a), Tsu-PR1 cells (b and c), DU145 for DU145 cells (d and e), PC-3 for PC-3 cells (f and g), and LNCaP for LNCaP.FGC cells (h and i). The number over each lane indicates the amount of protein ($\mu$) loaded in each well. The huMUC18 protein band is indicated with an open triangle. The numbers on the right-most lane indicate the protein molecular weight (kDa) rainbow markers (RPN800, Amershan).
Figure 7:
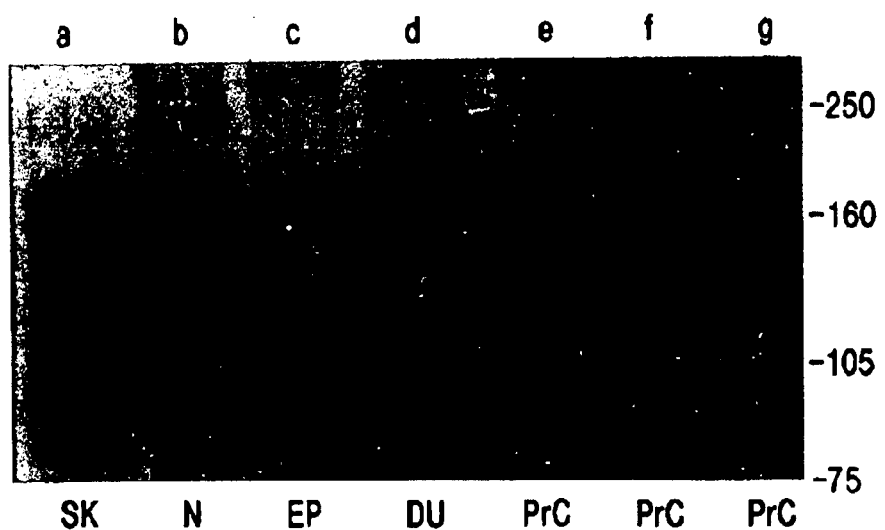
FIG. 7 shows the results of Western blot analysis of human MUC18 protein in normal prostatic gland, normal primary human prostatic epithelial cells, and tissues of a patient with malignant prostatic cancer. Cellular lysates were prepared from normal prostatic gland (b), cultured normal primary prostatic epithelial cells (c), and prostatic cancerous tissues from a patient with malignant prostatic cancers (e–g). Cellular extracts prepared from human SK-Mel-28 cells (a) and from DU 145 cells (d) were shown as the positive controls. 20 $\mu$g protein of each lysate was loaded per well. The numbers on the right-most lane indicate the protein molecular weight (kDa) rainbow markers (RPN800, Amersham).

Using the MUC18-specific antibody preparation from chickens after immunization with the purified human recombinant huMUC18 middle fragment protein, the present inventor has shown that these antibodies can react with the human MUC18 protein expressed in human prostate cancerous cell lines and prostatic cancerous tissues by Western blot analysis. The results showed that the human MUC18 protein was only expressed in three metastatic prostate cancer cell lines (Tsu-PR-1, DU145 and PC-3), but not in one non-metastatic cell line (LNCaP.FGC). These results are consistent with the Northern blot analysis of the expression of huMUC18 mRNA in these prostatic cancer cell lines, described herein. The human MUC18 protein was weakly expressed in normal prostatic epithelial cells and in normal prostate gland, but highly expressed in human cancerous prostatic tissues, as shown by Western blot analysis of the extracts prepared from these tissues. See FIG. 6 for the results of Western blot analysis.

Further immunohistochemical analysis revealed that huMUC18 is expressed in the membrane of the expected special cell types, such as metastatic melanoma tissues, endothelial cells, and smooth muscle cells. This indicates that the antibodies are very specific for huMUC18 antigen and work well with the formaldehyde-fixed, paraffin-embedded tissue sections. As expected, the antibodies did not react with any antigens of the normal secretory epithelial cells in the acini of the prostate gland. Interestingly, they react with the secretory epithelial cells in the acini of the prostate cancer tissues. The expression of human MUC18 protein (or antigen) only in cancerous epithelial cells, but not in normal epithelial cells, supports the use of human MUC18 as a diagnostic marker for the metastatic potential of prostate cancers.

Table 2 summarizes the results for MUC18 expression in four prostate cancer cell lines in comparison with pertinent results published by other groups. Expression of MUC18 in these cell lines is consistent with their low or no expression of E-cadherin and α-catenin and their extent of invasiveness in vitro and metastasis in nude mice. See FIG. 6 for Western blot analysis.

The present work has correlated relatively high levels of MUC18 with the ability of prostate cancer cells to metastasize. High levels of MUC18 expression were observed in the three metastatic prostate cancer cell lines TSU-PR1, DU145 and PC-3. MUC18 expression was not detectable in the LNCAP prostate cell line, which is not metastatic. Nonmetastatic prostate cancer cells and normal prostate cells produce no or barely detectable expression of MUC18 either as protein or mRNA. Experiments in which the LNCAP cell line is genetically engineered to express MUC18 at high levels demonstrate that when cells gain the capacity to express MUC18 at high levels, those cells gain the ability to metastasize. Experiments in which the non-metastatic prostate cancer cell line LNCaP.FGC is genetically engineered to express MUC18 at high levels demonstrate that when the cells gain the capacity to express MUC18 at high levels, the ability to metastasize is also gained. Thus, the relative level of MUC18 expression in prostate tumor tissue is correlated with the ability to metastasize, and measurement of MUC18 expression in prostate tumor biopsy tissue allows the medical practitioner to choose the most appropriate therapy for each prostate cancer patient, with high levels of MUC18 expression mandating an aggressive treatment strategy, likely including surgery, chemotherapy and/or radiation.

TABLE 2

| | RELATIVE LEVELS OF MUC18 EXPRESSION | | | | |
|---|---|---|---|---|---|
| | TSU-PR1 | DU145 | PC-3 | LNCAP | Reference |
| E-cadherin expression | 0 | 0.1 | 0.6 | 1.1 | Morton et al. (1993) Cancer Res. 53, 3585–3590 |
| α-catenin expression | none | none | none | yes | Morton et al. (1993) |
| Total RNA (MUC18) | yes | yes | yes | none | this work |
| tumor growth in nude mice | yes (2000) | yes (500) | Yes (1400) | yes (2000) | Passaniti et al. (1992) International J. Cancer 51, 318–324 |
| Metastasis in nude mice | yes | yes | yes | none | Lalani et al. (1992) Cancer Metastasis Rev. 16, 29–66 |

TABLE 2-continued

RELATIVE LEVELS OF MUC18 EXPRESSION

|  | TSU-PR1 | DU145 | PC-3 | LNCAP | Reference |
|---|---|---|---|---|---|
| Invasiveness in vitro | yes (220) | yes (25) | yes (20) | none | Passaniti et al. (1992) |

Monoclonal or polyclonal antibodies, preferably monoclonal, specifically reacting with MUC18, may be made by methods well known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York. Also, recombinant immunoglobulins may be produced by methods known in the art, including but not limited to, the methods described in U.S. Pat. No. 4,816,567. Monoclonal antibodies with affinities of $10^8$ $M^{-1}$, preferably $10^9$ to $10^{10}$ $M^{-1}$ or more, are preferred.

Antibodies (polyclonal or monoclonal) specific for MUC18 are useful, for example, as probes for screening DNA expression libraries or for detecting the presence (and relative amounts) of MUC18 in a test sample, for example, prostate tumor biopsy tissue or a tissue slice of a metastatic prostate cancer, or cells in culture which were derived from a primary prostate cancerous tumor or a metastatic prostate cancer tumor. Desirably, the results are normalized to cell number or to total cellular protein. Frequently, the polypeptides and antibodies are labeled by joining, either covalently or noncovalently, a substance which provides a detectable signal. Suitable labels include, but are not limited to, radionuclides, enzymes, substrates, cofactors, inhibitors, fluorescent agents, chemiluminescent agents, magnetic particles and the like. United States Patents describing the use of such labels include, but are not limited to, U.S. Pat. Nos. 3,817,837; 3,850,752; 3,939,350; 3,996,345; 4,277,437; 4,275,149; and 4,366,241.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part 1; Wu (ed.) (1979) *Meth Enzymol.* 68; Wu et al. (eds.) (1983) *Meth. Enzymol.* 100 and 101; Grossman and Moldave (eds.) *Meth Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*, Glover (ed.) (1985) *DNA Cloning* Vol. I and II Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

All references cited in the present application are incorporated by reference herein to the extent that they are not inconsistent with the present disclosure.

The following examples are provided for illustrative purposes, and are not intended to limit the scope of the invention as claimed herein. Any variations in the exemplified articles and/or methods which occur to the skilled artisan are intended to fall within the scope of the present invention.

EXAMPLES

Example 1

Recombinant MUC18 Production and Antibody Production

Figure 5:
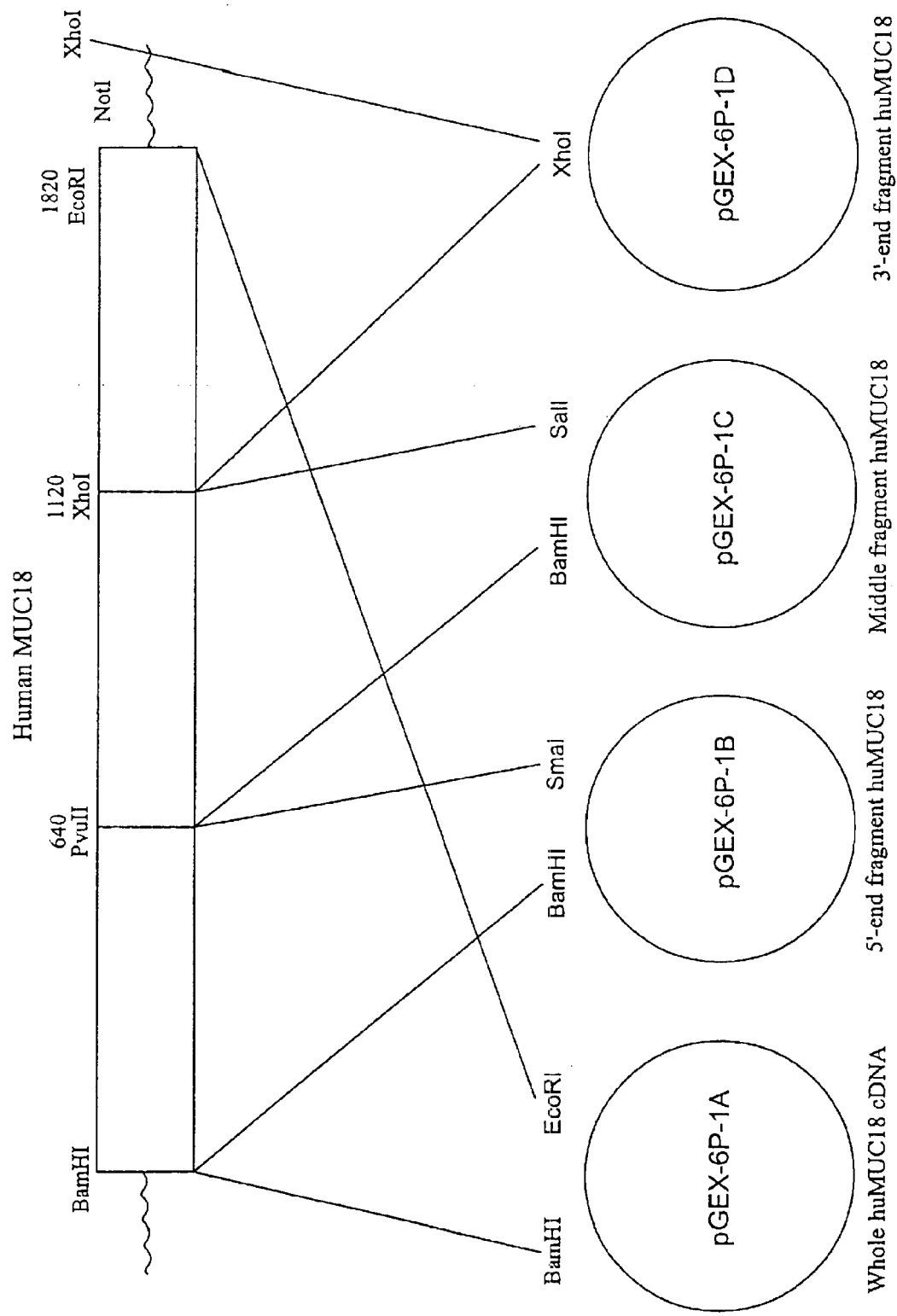
FIG. 5 provides diagrammatic illustrations of the whole cDNA sequence of human MUC18, its N-terminal fragment, middle fragment and C-terminal fragment, as cloned into the pGEX-6P-1 vector are provided. These fragments as cloned result in the expression of the N-terminal, middle and C-terminal fragments of the MUC18 protein. See also Tables 1A—1B for the locations of the relevant restriction sites in the cDNA sequence for human MUC18 and SEQ ID NO:1 for sequence.

The human MUC18 cDNA (1970 bp, RT-PCR amplified fragment) and three sub-fragments have been cloned in-phase in a GST-fusion protein expression system, pGEX-6p-1 (Pharmacia), which contains the glutathione-S-transferase (GST) coding region as an affinity-tag for the inserted foreign protein at its C-terminus. FIG. 1 and FIG. 5 show the four possible fusions: the whole region, the N-terminal fragment, the middle fragment, and the C-terminal fragment.

Only the middle fragment of the human MUC18 protein can be induced by IPTG to express in a high amount in *E. coli* K-12 strain BL-21. Thus, only this protein is further purified for immnunization. When culture $A_{600}$ reaches 0.6 (2 to 3 hours after 1/100 inoculation of an overnight culture in L-broth with ampicillin), the expression of the recombinant middle fragment of MUC18 protein fused to GST in recombinant *E. coli* is induced by addition of 0.1 mM of IPTG to 3-liter cultures (1.5 liters per 4-liter baffled flask). Two hours after addition of IPTG at 37° C., cells are harvested by centrifugion at 3,000 rpm (2,323×g) for 20 min in a horizontal HG-4L rotor in Sorvall RC-3 centrifuge. The cell pellet is suspended in 40 ml of ice-cold PBS (10 mM $Na_2HPO_4$, 1.8 mM $KH_2PO_4$, 2.7 mM KCl, and 140 mM NaCl, pH 7.3) and then lysed with a prechilled French pressure cell at 800 psi. The lysate is clarified by centrifugation for two to three times at 13,000 rpm (21,000×g) for 30 min in SS-34 rotor in Sorvall RC-2 centrifuge. The protein concentration of the clear crude lysate adjusted to 10 mg/ml protein (about 60 ml) was used as the starting material for purification. The recombinant MUC18 proteins are purified from the clear crude lysate by batchwise adsorption to the Glutathione-Sepharose 4B affinity resin (about 20 ml of 50% slurry) by inversion on an inversion shaker at room temperature for 30 min. The GST portion of the fusion protein mediates the binding of the protein to the resin via the glutathione. After twice washing with 10 volumes (50 ml per 5 ml packed resin) of 1×PBS and followed by twice washing with 1× PreCission protease cleavage buffer (50 mM TrisHCl, pH 7.0, 150 mM NaCl, 1 mM EDTA, 1 mM DTT) to remove unbound proteins, the fusion protein on the resin is cleaved with 100 units of HRV-3C protease (PreCission protease, 2 units/μl, from Pharmacia) by rocking on an inversion shaker for 16 hours at 4° C. The resin was spun down at 2,000 rpm for 10 min in a Sorvall RC-32 centrifuge. The supernatant and three washings (10 ml 1×PBS per 10 ml resin), which contain the recombinant MUC18 protein, are then combined and concentrated by centrifuging through a Centricon-30 (Millipore/Amicon). The purity of the protein is characterized by SDS-PAGE (8 to 10% polyacrylamide gel, slab gel). The 70 kDa contaminated protein is removed by passing through a Superdex 200 HR 10/30 column in 1×PBS (void volume about 7 ml for a 20 ml packed column), and the fractions containing the recombinant middle fragment MUC18 protein (22 kDa) (eluted at about 15.5 ml) were pooled. FIGS. 2A and 2B show the SDS-PAGE results or recombinant huMUC18 protein in the GST-fusion system.

Six mg of protein is sent to Lampire Biological Lab. (Pipersville, Pa.) for immunizing three chickens. The anti-MUC18 antibody titers are determined by ELISA assay using the purified recombinant MUC18 as the antigen. Eggs collected during the period of high serum antibody titers are used for purification of chicken immunoglobulin IgY.

To confirm the association between MUC18 expression and metastatic ability of prostate cancer cells, the human MUC18 coding sequence is introduced into a non-metastatic, non-expressing human prostate cancer cell line (LNCAP), and clones with different levels of expression of MUC18 are isolated.

The human MUC18 cDNA has been cloned into pCR3.1 Uni (Promega, Madison, Wis.), a mammalian expression vector in which high levels of gene expression are driven by the human CMV-IE promoter. The human MUC18 cDNA is also cloned into a murine anmphitrophic retrovirus expression vector, e.g. pZipNeoSVX [Cepko et al. (1984) *Cell* 37, 1053–1062] or LXSN [Miller and Rosman (1989) *BioTechniques* 7, 980–990], in which LTR drives gene expression.

These MUC18 recombinant vectors are used to transfect a human prostate cancer cell line which does not express MUC18, for example the LNCaP.FGC cell line [Umbas et al. (1992) *Cancer Res.* 52, 5104–5109; Iizumi et al (1987) *J. Urol.* 137: 1304–1306]. The vectors are introduced into the cultured cells by lipofection [Felgner et al. (1987) *Proc. Natl. Acad. Sci. USA* 84, 7413–7417] or by electroporation [Potter, H. (1988) *Anal. Biochem.* 174:361–373]. G418-resistant clones are selected and purified [Yuo et al. (1992) *Intervirol.* 34, 94–104] in view of the kanamycin resistance coding sequence expressed under the control of the SV40 promoter in each of the vectors. Relative expression levels of MUC18 expression in different clones are determined by western blotting with polyclonal antibodies (described herein). Metastatic abilities are determined as described herein.

Example 2
Determination of Metastatic Ability of Prostate Cancer Cells

The degree of motility and the invasiveness of prostate cancer cells are quantitated using published methods [Tucker et al. (1994) *Eur. J. Cell Biol.* 58, 28–290; Repesh, L. A. (1989) *Invasion and Metastasis* 9, 192–208]. The Costar transwell chamber contains an inner well with a porous polycarbonate membrane, with 3 μm pore sizes in the bottom of the well. This is tightly fitted to the outer well.

To determine the motility of human prostate cancer cells, 0.5×10$^5$ cells are seeded in the top well. The cells remain on the top well because the poly carbonate membrane only allows medium to pass through freely. After seeding and attachment, the cells in the top well gradually migrate through the pores in the polycarbonate membrane to the bottom side of the membrane. Eventually some cells establish growth at the bottom side of the membrane. When the pore size of the membrane is about 3 μm, it somewhat slows the movement of the cells from the top side of the membrane to the bottom side. Motility of the cells is measured over the next several consecutive days. The rate of motility of a given cell line can be determined quantitatively by counting the cell number at the bottom of the membrane after trypsinization. Using this in vitro method, the motility rates of PC3and PC-huMUC18 human prostate cancer cells, with and without an over-expression of the human MUC18 protein, respectively, are determined and compared.

For the invasiveness of the prostate cancer cells, a similar kind of chamber is used, except before seeding the cells to the top well, the polycarbonate membrane is pre-coated with matrigel that contains protein components of the basal membranes of blood vessels. When the concentration of matrigel is correct, the membrane thus formed is thick enough to form a barrier to stop the cells from penetrating immediately, but is thin enough to allow cells to gradually invade through the membrane and migrate to the bottom of the membrane. Matrigel, which contains protein components of the base membrane of blood cell membrane, such as laminin, collagen type IV, entactin (nedogen), and heparin sulfate proteoglycan, is available commercially through Collaborative Research (Bedford, Mass.). Each filter in each 6.5 mm well is coated with 100 μl of a 1:20 dilution of commercial Matrigel in cold DMEM (about 30 μg per filter). Using a similar method of counting the cells, which grow and attach to the bottom of the membrane, the rate of invasiveness of a given cell line can be quantitated [Repesh, La. (1989) supra]. To count the cells at the bottom of the membrane, the bottom of the membrane is treated with trypsin to detach the cells, and the cell number is counted directly using a Hemacytometer, or the cells on the membrane is stained with trypan blue and counted directly using a microscope. Alternatively, the cells are labeled with 0.6 μCi of $^{125}$I-iododeoxyuridine (5 Ci/mg) for 18–24 h (about 95% of cells) and seeded to the top of the transwell chamber. After 72 h of invasion, the cells at the bottom and the cells on the top are trypsinized. The total input radioactivity is determined and compared to the radioactivities associated with cells from the top and bottom chambers. In this way the percentage of cells invading through the membrane can be accurately quantitated. Invasion rate can thus be determined (Repesh, LA. (1989) *Invasion & Metast.* 9:192–208]. This type of in vitro test has been demonstrated to produce results in agreement with that of the in vivo animal tests [Repesh, LA. (1989) supra]. Using this in vitro method, the invasion rates of LNCAP and LNCAP-huMUC18 transformed or transfected to express MUC18 human prostate cells, with and without over-expression of the human MUC18 protein, respectively, are determined and compared.

For comparison, the metastasis rates of these prostate cells are also tested in vivo in athymic nude mice [van-Weerden et al. (1996) *Am. J. Pathol* 149, 1055–1062]. The effect of the different expression levels of human MUC18 in prostate cancer cells on metastatic ability of different clones is determined. Similar pairs of cells as used for in vitro assay are also used in animal tests. The cells are implanted subcutaneously into nude mice. The size of tumors after different times are measured. The time and extent of the tumor cell metastases to bone or to other organs are investigated [van Weerden et al. (1996) supra].

The experiments set forth above confirm that the relative level of MUC18 expression in prostate cancer cells correlates positively with metastatic ability.

Example 3
Transcriptional Expression of MUC18

Total cell RNA is prepared from cell lines or from prostate tumor tissue with the method of one step acid-guanidinium-thiocyanate-phenol-chloroform extraction [Chomczyuski and Sacchi (1987) *Anal. Biochem.* 162, 156–159]. We have shown that this method consistently yields good quality RNA for RT-PCR. Poly(A)+RNA is prepared from total RNA by purifying through an oligo(dT)-cellulose column [Aviv and Leder (1 972) *J. Molec. Biol.* 134, 743; Wu et al. (1985) *Int. J. Biochem.* 17, 355–363].

Northern hybridization technology is used to determine MUC18 mRNA levels expressed in the four prostate cancer cell lines [Ausubel et al. (1987) *Current Protocols in Molecular Biology*, Section 4]. Total RNA is extracted from cell preparations, electrophoretically separated in a formaldehyde-impregnated agarose gel, blotted and hybridized to a $^{32}$P-labeled human MUC18 cDNA [Feinberg and Vogelstein (1983) *Anal. Biochem.* 132, 6–13]. Relative levels of MUC18 mRNA are detected by radioautography. The amount of RNA loaded and transferred is estimated by the intensities of the 28S and 16S bands in each lane.

Alternately, G3PDH mRNA can be estimated using a G3PDH-specific probe or 28S and 18S probes after stripping the MUC18-specific probe.

Quantitative RT-PCR methodology [Innis et al. (1990) PCR Protocols, Academic Press; Quantitative RT-PCR (1993) Methods and Applications Book #3, Clontech, Palo Alto, Calif.]. Human Sk-Mel-28 cells are used as positive control for this method.

Because the quantity of mRNA from a small amount of tissue is small, quantitative RT-PCR is used for quantifying MUC18 mRNA expression in tissues [Innis et al. (1990) supra]. The isolation kit from Boehringer-Mannheim (Indianapolis, Ind.) using magnetic beads is suitable for obtaining a small amount of poly(A+RNA from prostate tissue. The quality of mRNA isolated with this kit is also excellent for translation and RT-PCR. The quantitative RT-PCR method is first established from using MRNA of cultured cells, as described above, and then is used for quantifying the expression of MUC18 mRNA in different prostate cancer tissues.

The RT step is standard: a 20 μl RT reaction contains 1 μg of poly(A)+RNA from the human melanoma cell line, SK-Mel-28, as template, 0.5 μg of oligo(dT)$_{16}$ as primer (Promega), 2 μl of 10×OX AMV-RT buffer (Promega, Madison, Wis.), 2 units of AMV-reverse transcriptase, 5 MM MgCl$_2$, 1 mM of dNTP mix (Promega), 1 unit of RNase inhibitor (Promega), and 50 μg/ml of acetyl BSA. The reaction was carried out at 42 to 48° C. for one hour, and heated at 99° C. for 5 min.

A 20 μl PCR reaction contained 2 μl of RT reaction mixture (containing the first-strand cDNA), 2 μl each of the two primers (20 pm/μl), 0.01 mM dNTPs, 1 μg of acetyl BSA, 2 μl of 10×PCR buffer with 15 mM MgCl$_2$ (Promega), and 0.5 units of Taq DNA polymerase (Promega, 5 units/μl). PCR cycles are as follows:

Hot start at 94° C. 5 min, 80° C. 30 sec 29 cycles of 94° C. 30 sec, 64–66° C. 30 sec, and 72° C. 2 min 1 cycle of 94° C. 30 sec, 64–66° C. 30 sec, and 72° C. 60 min The sequences of the primers for amplification of the human MUC18 cDNA from poly(A)+RNA of human melanoma cell line SK-Mel-28 are as follows:

BF1 27-mer
5'-CTCGGGATCCATGGGGCTTCCCAGGCT (SEQ ID NO:9)

ER6A 25-mer
5'-TCGGGGCTAATGCCTCAGATCGATG (SEQ ID NO:10)

Example 4
Immnunofluorescence Assay for MUC18

Where the anti-human MUC18 antibodies are made in chicken, fluorescence-tagged anti-chicken IgG are used for immunofluorescent staining. Tissue culture cells, or normal or cancer prostate tissue samples are fixed, and first reacted with the anti-human MUC18 antibodies, washed, and then reacted with the fluorescence-tagged rabbit anti-chicken antibodies [Umbas et al. (1 992) Canc. Res. 52, 5104–5109]. The presence of human MUC18 on the surface of these cells or tissues readily detected using UV-fluorescence microscopy.

Human melanoma cells, Sk-Mel-28 (ATCC HTB 72), which express MUC18 a high level of MUC18 are used as the positive control. Human melanoma cells, WM115 (ATCC CRL 1675) which express no MUC18, are used as the negative control. Three human ho prostate cancer cell lines, LNCap.FGC, PC-3, and DU145 are available from American Type Culture Collection, Rockville, Md., as ATCC CRL 1740, ATCC CRL 1435 and ATCC HTB 81, respectively. One other cell line, TSU-PR1, isolated by Dr. Iizumi in Japan [Uizumi et al. (1987) *J. Urol.* 137, *J. Urol.* 137:1304–1306] and provided by Dr. John T. Isaacs, John Hopkins University, Baltimore, Md.] was tested. TSU-PR1 cells are more metastatic than the other three cell lines [Graff et al. (1995) *Cancer Res.* 55, 5195–5199].

All four cell lines are grown as monolayer cultures in a 37° C. incubator with an atmosphere of 5% $CO_2$. Tsu-PR1 and LNCap.FGC cells are grown in RPMI 1640 supplemented with 10% fetal bovine serum. PC-cells are grown in F12K medium with 10% fetal bovine serum. DU145 cells are grown in EMEM medium supplemented with pyruvate, extra non-essential amino acids and vitamins, and 10% fetal bovine serum.

Biopsy samples are taken, fixed and subjected to immunoassay using polyclonal antibody specific for human MUC18 described hereinabove, as described in Wood et al. (1994) *cancer* 74:2533–2540.

I claim:

1. A method of identifying a metastatic prostate cancer cell consisting essentially of measuring expression of the MUC18 coding sequence in a prostate cancer cell, wherein the expression of the MUC18 coding sequence is determined by immunoassay using antibodies specific for an epitope of the MUC18 polypeptide consisting of the amino acid sequence set forth in SEQ ID NO: 2, whereby a greater expression of the MUC18 coding sequence in said prostate cancer cell compared to that in a normal prostate cell indicates the prostate cancer cell is metastatic.

2. A method of identifying a malignant prostate cancer cell consisting essentially of measuring expression of the MUC18 coding sequence in a prostate cancer cell, wherein the expression of the MUC18 coding sequence is determined by immunoassay using antibodies specific for an epitope of the MUC18 polypeptide consisting of the amino acid sequence set forth in SEQ ID NO: 2, whereby a greater expression of the MUC18 coding sequence in said prostate cancer cell compared to that in a normal prostate cell indicates the prostate cancer cell is malignant.

3. The method of claim 1 or 2, wherein said prostate cancer cell is from a biopsy tissue sample from a patient.

4. The method of claim 1 or 2, wherein the epitope of the MUC18 polypeptide is contained in the middle portion of the MUC18 polypeptide consisting of amino acid residues 211–376 of the amino acid sequence as set forth in SEQ ID NO: 2.

5. The method of claim 1 or 2, wherein said prostate cancer cell is a cell line cell.

* * * * *